(12) United States Patent
Zhang et al.

(10) Patent No.: US 7,371,845 B2
(45) Date of Patent: May 13, 2008

(54) MAGE-A3 PEPTIDES PRESENTED BY HLA CLASS II MOLECULES

(75) Inventors: Yi Zhang, Brussels (BE); Pascal Chaux, Thurey (FR); Thierry Boon-Falleur, Brussels (BE); Pierre Van Der Bruggen, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 88 days.

(21) Appl. No.: 11/439,334

(22) Filed: May 23, 2006

(65) Prior Publication Data

US 2006/0211091 A1 Sep. 21, 2006

Related U.S. Application Data

(62) Division of application No. 09/860,840, filed on May 18, 2001, now Pat. No. 7,049,413.

(51) Int. Cl.
*C07H 21/04* (2006.01)
*C12N 15/00* (2006.01)
*C12N 5/02* (2006.01)

(52) U.S. Cl. .................. 536/23.5; 435/325; 435/320.1

(58) Field of Classification Search ..................... None
See application file for complete search history.

(56) References Cited

U.S. PATENT DOCUMENTS

| 5,342,774 A | 8/1994 | Boon et al. |
| 5,405,940 A | 4/1995 | Boon et al. |
| 5,585,461 A | 12/1996 | Townsend et al. |
| 5,591,430 A | 1/1997 | Townsend et al. |
| 5,965,535 A | 10/1999 | Chaux et al. |

FOREIGN PATENT DOCUMENTS

| GB | 2351905 A | 1/2001 |
| WO | WO 92/20356 | 11/1992 |
| WO | WO 94/20127 | 9/1994 |
| WO | WO 94/23031 | 10/1994 |
| WO | WO 95/25740 | 9/1995 |
| WO | WO 97/13858 A2 | 4/1997 |
| WO | WO 98/04582 | 2/1998 |
| WO | WO 99/14326 | 3/1999 |
| WO | WO 99/45954 | 9/1999 |
| WO | WO 00/20581 | 4/2000 |
| WO | WO 00/52045 A | 5/2003 |
| WO | WO 03/040165 | 5/2003 |

OTHER PUBLICATIONS

De Plaen et al., "Structure, Chromosomal Localization, and Expression of 12 Genes of the Mage Family," *Immunogenetics* vol. 40 No. 5, pp. 360-369.
Traversari et al., *Immunogenetics* 35:145-152 (1992).
Van Der Bruggen et al., *Science* 254:1643-1647 (1991).
Topalian, *Curr. Opin. Immunol*, 6:741-745 (1994).
Yee et al., *J. Immunol.*, 157:4079-4086 (1996).
Topalian et al., *J. Exp. Med* 183:1965-1971 (1996).
Sanderson et al., *Proc. Nat'l. Acad. Sci.* USA 92:7217-7221 (1995).
Wu et al., *Proc Nat'l Acad Sci* USA 92:11671-11675 (1995).
Gaugler et al., *J. Exp. Med.* 179:921-930 (1994).
Van Der Bruggen et al., *Eur. J. Immunol.* 24:3038-3043 (1994).
Herman et al., *Immunogenetics* 43:377-383 (1996).
Engelhard, *Annu. Rev. Immunol.*, 12:181-207 (1994).
Chicz et al., *J. Exp. Med.*, 178:27-47 (1993).
Chaux et al., "Identification of Mage-3 Epitopes Presented by HLA-DR Molecules to CD4+ T Lymphocytes," *J. Exp. Med.* vol. 189, No. 5, Mar. 1, 1999, pp. 767-777.
Spatola, A.F., *Chem. and Biochem. of Amino Acids, Peptides, and Proteins* 7:267-357.
Thomson et al., *J. Virol.* 72:2246-2252 (1998).
Manici, S. et al., "Melanoma cells present a MAGE-3 epitope to CD4' cytotoxic T cells in association with histocompatibility leukocyte antigen DR11" J. Exp. Med., Mar. 1, 1999, vol. 189, No. 5, pp. 871-876.
Zhang, Y., et al., "A MAGE-3 peptide presented by HLA-DR1 to CD4+ T cells that were isolated from a melanoma patient vaccinated with MAGE-3 protein." J. Immunol. Jul. 1, 2003, vol. 171, No. 1, pp. 219-225.
Germain, R.N., *Fundamental Immunolgy*, Fourth Edition, W.E. Paul, editor [1999] Lippincott-Raven Press, Philadelphia, pp. 287-340.
Schultz, E.S. et al., "A Mage-A3 peptide presented by HLA-DP4 is recognized on tumor cells by CD4+ cytolytic T lymphocytes," *Cancer Res.* Nov. 15, 2000, vol. 60, No. 22, pp. 6572-6275.
Reynolds, S.R. et al., *Int. J. Cancer* (Sep. 1997) 72(6):972-976.
Smilek, D.E. et al., *Proc. Nat. Acad. Sci.* (USA) (Nov. 1991) 88:9633-9637.

*Primary Examiner*—Christina Chan
*Assistant Examiner*—F. Pierre VanderVegt
(74) *Attorney, Agent, or Firm*—Wolf, Greenfield & Sacks, P.C.

(57) ABSTRACT

The invention describes HLA class II binding peptides encoded by the MAGE-A3 tumor associated gene, as well as nucleic acids encoding such peptides and antibodies relating thereto. The peptides stimulate the activity and proliferation of CD4+ T lymphocytes. Methods and products also are provided for diagnosing and treating conditions characterized by expression of the MAGE-A3 gene.

20 Claims, 4 Drawing Sheets

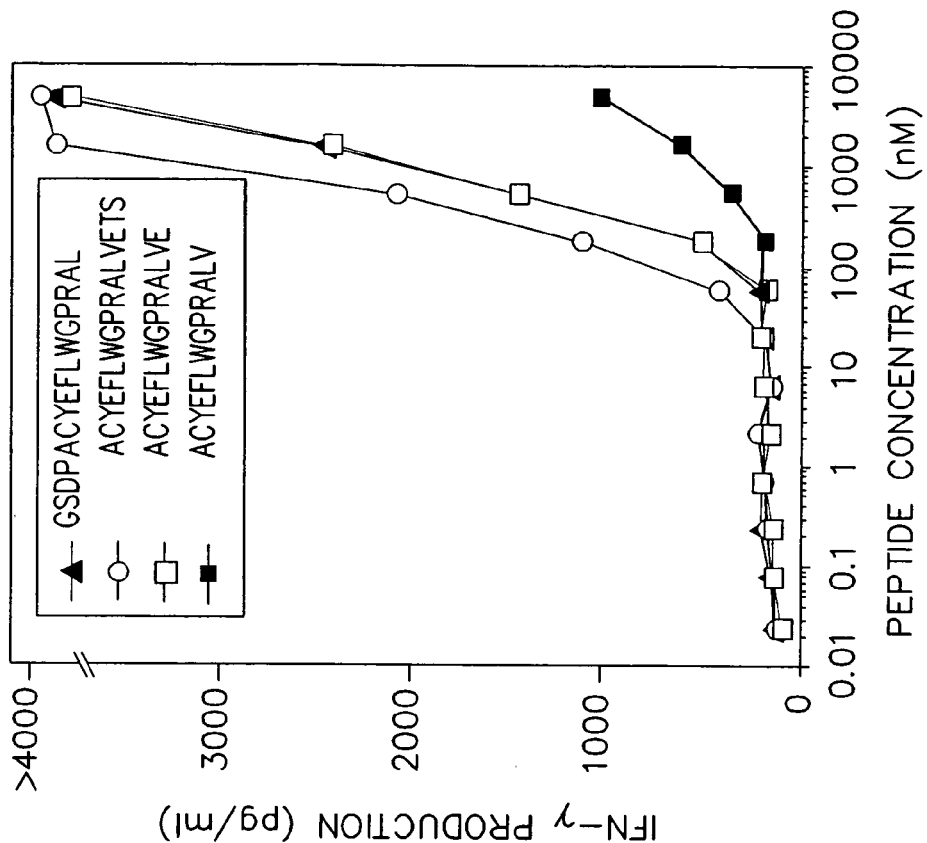
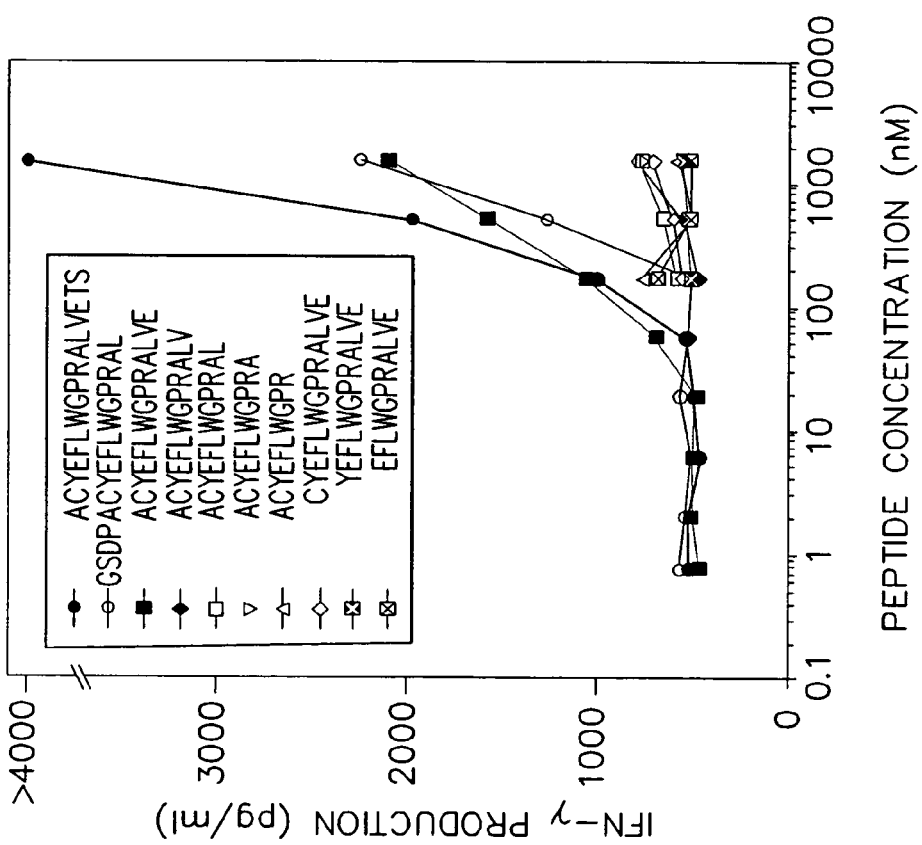

SEQUENCE LISTING

```
<160> NUMBER OF SEQ ID NOS: 18

<210> SEQ ID NO 1
<211> LENGTH: 4204
<212> TYPE: DNA
<213> ORGANISM: Homo sapiens
<220> FEATURE:
<221> NAME/KEY: CDS
<222> LOCATION: (2465)..(3409)

<400> SEQUENCE: 1
acgcaggcag tgatgtcacc cagaccacac cccttccccc aatgccactt caggggtac      60 tcagagtcag agacttggtc tgaggggagc agaagcaatc tgcagaggat ggcggtccag     120
gctcagccag gcatcaactt caggaccctg agggatgacc gaaggccccg cccacccacc     180
cccaactccc ccgaccccac caggatctac agcctcagga cccccgtccc aatccttacc     240
ccttgcccca tcaccatctt catgcttacc tccacccca tccgatcccc atccaggcag      300
aatccagttc caccctgcc cggaacccag ggtagtaccg ttgccaggat gtgacgccac      360
tgacttgcgc attggaggtc agaagaccgc gagattctcg ccctgagcaa cgagcgacgg     420
cctgacgtcg gcggagggaa gccggcccag gctcggtgag gaggcaaggt aagacgctga     480
gggaggactg aggcgggcct cacctcagac agagggcctc aaataatcca gtgctgcctc     540
tgctgccggg cctgggccac cccgcagggg aagacttcca ggctgggtcg ccactacctc     600
accccgccga ccccgccgc tttagccacg gggaactctg gggacagagc ttaatgtggc      660
cagggcaggg ctggttagaa gaggtcaggg cccacgctgt ggcaggaatc aaggtcagga     720
ccccgagagg gaactgaggg cagcctaacc accaccctca ccaccattcc cgtcccccaa     780
```

-continued

```
cacccaaccc caccccatc ccccattccc atccccaccc ccaccctat cctggcagaa      840 tccgggcttt gccctggta tcaagtcacg gaagctccgg gaatggcggc caggcacgtg      900
agtcctgagg ttcacatcta cggctaaggg agggaagggg ttcggtatcg cgagtatggc      960
cgttgggagg cagcgaaagg gcccaggcct cctggaagac agtggagtcc tgaggggacc     1020
cagcatgcca ggacaggggg cccactgtac ccctgtctca aaccgaggca cctttcatt      1080 cggctacggg aatcctaggg atgcagaccc acttcagcag ggggttgggg cccagccctg     1140
cgaggagtca tggggaggaa gaagagggag gactgagggg accttggagt ccagatcagt     1200
ggcaaccttg ggctgggga tgctgggcac agtggccaaa tgtgctctgt gctcattgcg      1260
ccttcagggt gaccagagag ttgagggctg tggtctgaag agtgggactt caggtcagca     1320
gagggaggaa tccaggatc tgcagggccc aaggtgtacc cccaagggc ccctatgtgg       1380 tggacagatg cagtggtcct aggatctgcc aagcatccag gtgaagagac tgagggagga     1440
ttgagggtac ccctgggaca gaatgcggac tgggggcccc ataaaaatct gccctgctcc     1500
tgctgttacc tcagagagcc tgggcagggc tgtcagctga ggtccctcca ttatcctagg     1560
atcactgatg tcagggaagg ggaagccttg gtctgagggg gctgcactca gggcagtaga     1620
gggaggctct cagaccctac taggagtgga ggtgaggacc aagcagtctc ctcacccagg     1680
gtacatggac ttcaataaat ttggacatct ctcgttgtcc tttccgggag gacctgggaa     1740
tgtatggcca gatgtgggtc ccctcatgtt tttctgtacc atatcaggta tgtgagttct     1800
tgacatgaga gattctcagg ccagcagaag ggagggatta ggccctataa ggagaaaggt     1860
gagggccctg agtgagcaca gaggggatcc tccacccccag tagagtgggg acctcacaga    1920
gtctggccaa ccctcctgac agttctggga atccgtggct gcgtttgctg tctgcacatt     1980
gggggcccgt ggattcctct cccaggaatc aggagctcca ggaacaaggc agtgaggact     2040
tggtctgagg cagtgtcctc aggtcacaga gtagagggg ctcagatagt gccaacggtg      2100
aaggtttgcc ttggattcaa accaagggcc ccacctgccc cagaacacat ggactccaga     2160
gcgcctggcc tcaccctcaa tactttcagt cctgcagcct cagcatgcgc tggccggatg     2220
taccctgagg tgccctctca cttcctcctt caggttctga ggggacaggc tgacctggag     2280
gaccagaggc ccccggagga gcactgaagg agaagatctg taagtaagcc tttgttagag     2340
cctccaaggt tccattcagt actcagctga ggtctctcac atgctccctc tctcccccagg    2400 ccagtgggtc tccattgccc agctcctgcc cacactcccg cctgttgccc tgaccagagt     2460 catc atg cct ctt gag cag agg agt cag cac tgc aag cct gaa gaa ggc     2509
     Met Pro Leu Glu Gln Arg Ser Gln His Cys Lys Pro Glu Glu Gly
     1               5                   10                  15 ctt gag gcc cga gga gag gcc ctg ggc ctg gtg ggt gcg cag gct cct     2557
Leu Glu Ala Arg Gly Glu Ala Leu Gly Leu Val Gly Ala Gln Ala Pro
            20                  25                  30 gct act gag gag cag gag gct gcc tcc tcc tct tct act cta gtt gaa     2605
Ala Thr Glu Glu Gln Glu Ala Ala Ser Ser Ser Ser Thr Leu Val Glu
        35                  40                  45 gtc acc ctg ggg gag gtg cct gct gcc gag tca cca gat cct ccc cag     2653
Val Thr Leu Gly Glu Val Pro Ala Ala Glu Ser Pro Asp Pro Pro Gln
    50                  55                  60 agt cct cag gga gcc tcc agc ctc ccc act acc atg aac tac cct ctc     2701
Ser Pro Gln Gly Ala Ser Ser Leu Pro Thr Thr Met Asn Tyr Pro Leu
65                  70                  75 tgg agc caa tcc tat gag gac tcc agc aac caa gaa gag gag ggg cca     2749
Trp Ser Gln Ser Tyr Glu Asp Ser Ser Asn Gln Glu Glu Glu Gly Pro
80                  85                  90                  95
```

| | | |
|---|---|---|
| agc acc ttc cct gac ctg gag tcc gag ttc caa gca gca ctc agt agg<br>Ser Thr Phe Pro Asp Leu Glu Ser Glu Phe Gln Ala Ala Leu Ser Arg<br>100 105 110 | 2797 | |
| aag gtg gcc gag ttg gtt cat ttt ctg ctc ctc aag tat cga gcc agg<br>Lys Val Ala Glu Leu Val His Phe Leu Leu Leu Lys Tyr Arg Ala Arg<br>115 120 125 | 2845 | |
| gag ccg gtc aca aag gca gaa atg ctg ggg agt gtc gtc gga aat tgg<br>Glu Pro Val Thr Lys Ala Glu Met Leu Gly Ser Val Val Gly Asn Trp<br>130 135 140 | 2893 | |
| cag tat ttc ttt cct gtg atc ttc agc aaa gct tcc agt tcc ttg cag<br>Gln Tyr Phe Phe Pro Val Ile Phe Ser Lys Ala Ser Ser Ser Leu Gln<br>145 150 155 | 2941 | |
| ctg gtc ttt ggc atc gag ctg atg gaa gtg gac ccc atc ggc cac ttg<br>Leu Val Phe Gly Ile Glu Leu Met Glu Val Asp Pro Ile Gly His Leu<br>160 165 170 175 | 2989 | |
| tac atc ttt gcc acc tgc ctg ggc ctc tcc tac gat ggc ctg ctg ggt<br>Tyr Ile Phe Ala Thr Cys Leu Gly Leu Ser Tyr Asp Gly Leu Leu Gly<br>180 185 190 | 3037 | |
| gac aat cag atc atg ccc aag gca ggc ctc ctg ata atc gtc ctg gcc<br>Asp Asn Gln Ile Met Pro Lys Ala Gly Leu Leu Ile Ile Val Leu Ala<br>195 200 205 | 3085 | |
| ata atc gca aga gag ggc gac tgt gcc cct gag gag aaa atc tgg gag<br>Ile Ile Ala Arg Glu Gly Asp Cys Ala Pro Glu Glu Lys Ile Trp Glu<br>210 215 220 | 3133 | |
| gag ctg agt gtg tta gag gtg ttt gag ggg agg gaa gac agt atc ttg<br>Glu Leu Ser Val Leu Glu Val Phe Glu Gly Arg Glu Asp Ser Ile Leu<br>225 230 235 | 3181 | |
| ggg gat ccc aag aag ctg ctc acc caa cat ttc gtg cag gaa aac tac<br>Gly Asp Pro Lys Lys Leu Leu Thr Gln His Phe Val Gln Glu Asn Tyr<br>240 245 250 255 | 3229 | |
| ctg gag tac cgg cag gtc ccc ggc agt gat cct gca tgt tat gaa ttc<br>Leu Glu Tyr Arg Gln Val Pro Gly Ser Asp Pro Ala Cys Tyr Glu Phe<br>260 265 270 | 3277 | |
| ctg tgg ggt cca agg gcc ctc gtt gaa acc agc tat gtg aaa gtc ctg<br>Leu Trp Gly Pro Arg Ala Leu Val Glu Thr Ser Tyr Val Lys Val Leu<br>275 280 285 | 3325 | |
| cac cat atg gta aag atc agt gga gga cct cac att tcc tac cca ccc<br>His His Met Val Lys Ile Ser Gly Gly Pro His Ile Ser Tyr Pro Pro<br>290 295 300 | 3373 | |
| ctg cat gag tgg gtt ttg aga gag ggg gaa gag tga gtctgagcac<br>Leu His Glu Trp Val Leu Arg Glu Gly Glu Glu<br>305 310 | 3419 | |
| gagttgcagc cagggccagt gggagggggt ctgggccagt gcaccttccg gggccgcatc | 3479 | |
| ccttagtttc cactgcctcc tgtgacgtga ggcccattct tcactctttg aagcgagcag | 3539 | |
| tcagcattct tagtagtggg tttctgttct gttggatgac tttgagatta ttctttgttt | 3599 | |
| cctgttggag ttgttcaaat gttcctttta acggatggtt gaatgagcgt cagcatccag | 3659 | |
| gtttatgaat gacagtagtc acacatagtg ctgtttatat agtttaggag taagagtctt | 3719 | |
| gttttttact caaattggga aatccattcc attttgtgaa ttgtgacata ataatagcag | 3779 | |
| tggtaaaagt atttgcttaa aattgtgagc gaattagcaa taacatacat gagataactc | 3839 | |
| aagaaatcaa aagatagttg attcttgcct tgtacctcaa tctattctgt aaaattaaac | 3899 | |
| aaatatgcaa accaggattt ccttgacttc tttgagaatg caagcgaaat taaatctgaa | 3959 | |
| taaataattc ttcctcttca ctggctcgtt tcttttccgt tcactcagca tctgctctgt | 4019 | |
| gggaggccct gggttagtag tggggatgct aaggtaagcc agactcacgc ctacccatag | 4079 | |
| ggctgtagag cctaggacct gcagtcatat aattaaggtg gtgagaagtc ctgtaagatg | 4139 | | tagaggaaat gtaagagagg ggtgagggtg tggcgctccg ggtgagagta gtggagtgtc    4199 agtgc                                                                4204

<210> SEQ ID NO 2
<211> LENGTH: 314
<212> TYPE: PRT
<213> ORGANISM: Homo sapiens

<400> SEQUENCE: 2

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 3
<211> LENGTH: 16
<212> TYPE: PRT
<213> ORGANISM: Homo sapiens

```
<400> SEQUENCE: 3

Gly Ser Asp Pro Ala Cys Tyr Glu Phe Leu Trp Gly Pro Arg Ala Leu
1               5                   10                  15

<210> SEQ ID NO 4
<211> LENGTH: 16
<212> TYPE: PRT
<213> ORGANISM: Homo sapiens

<400> SEQUENCE: 4

Ala Cys Tyr Glu Phe Leu Trp Gly Pro Arg Ala Leu Val Glu Thr Ser
1               5                   10                  15

<210> SEQ ID NO 5
<211> LENGTH: 48
<212> TYPE: DNA
<213> ORGANISM: Homo sapiens

<400> SEQUENCE: 5
ggcagtgatc ctgcatgtta tgaattcctg tggggtccaa gggccctc              48

<210> SEQ ID NO 6
<211> LENGTH: 48
<212> TYPE: DNA
<213> ORGANISM: Homo sapiens

<400> SEQUENCE: 6
gcatgttatg aattcctgtg ggtccaagg gccctcgttg aaaccagc               48

<210> SEQ ID NO 7
<211> LENGTH: 14
<212> TYPE: PRT
<213> ORGANISM: Homo sapiens

<400> SEQUENCE: 7

Ala Cys Tyr Glu Phe Leu Trp Gly Pro Arg Ala Leu Val Glu
1               5                   10

<210> SEQ ID NO 8
<211> LENGTH: 13
<212> TYPE: PRT
<213> ORGANISM: Homo sapiens

<400> SEQUENCE: 8

Ala Cys Tyr Glu Phe Leu Trp Gly Pro Arg Ala Leu Val
1               5                   10

<210> SEQ ID NO 9
<211> LENGTH: 12
<212> TYPE: PRT
<213> ORGANISM: Homo sapiens

<400> SEQUENCE: 9

Ala Cys Tyr Glu Phe Leu Trp Gly Pro Arg Ala Leu
1               5                   10

<210> SEQ ID NO 10
<211> LENGTH: 11
<212> TYPE: PRT
<213> ORGANISM: Homo sapiens

<400> SEQUENCE: 10

Ala Cys Tyr Glu Phe Leu Trp Gly Pro Arg Ala
1               5                   10
```

```
<210> SEQ ID NO 11
<211> LENGTH: 10
<212> TYPE: PRT
<213> ORGANISM: Homo sapiens

<400> SEQUENCE: 11

Ala Cys Tyr Glu Phe Leu Trp Gly Pro Arg
1               5                   10

<210> SEQ ID NO 12
<211> LENGTH: 13
<212> TYPE: PRT
<213> ORGANISM: Homo sapiens

<400> SEQUENCE: 12

Cys Tyr Glu Phe Leu Trp Gly Pro Arg Ala Leu Val Glu
1               5                   10

<210> SEQ ID NO 13
<211> LENGTH: 12
<212> TYPE: PRT
<213> ORGANISM: Homo sapiens

<400> SEQUENCE: 13

Tyr Glu Phe Leu Trp Gly Pro Arg Ala Leu Val Glu
1               5                   10

<210> SEQ ID NO 14
<211> LENGTH: 11
<212> TYPE: PRT
<213> ORGANISM: Homo sapiens

<400> SEQUENCE: 14

Glu Phe Leu Trp Gly Pro Arg Ala Leu Val Glu
1               5                   10

<210> SEQ ID NO 15
<211> LENGTH: 42
<212> TYPE: DNA
<213> ORGANISM: Homo sapiens

<400> SEQUENCE: 15
gcatgttatg aattcctgtg gggtccaagg gccctcgttg aa                          42

<210> SEQ ID NO 16
<211> LENGTH: 15
<212> TYPE: PRT
<213> ORGANISM: Homo sapiens

<400> SEQUENCE: 16

Ala Cys Tyr Glu Phe Leu Trp Gly Pro Arg Ala Leu Val Glu Thr
1               5                   10                  15

<210> SEQ ID NO 17
<211> LENGTH: 24
<212> TYPE: DNA
<213> ORGANISM: Homo sapiens

<400> SEQUENCE: 17
ccctcatgag ggcaggtgcc accg                                              24

<210> SEQ ID NO 18
<211> LENGTH: 31
<212> TYPE: DNA
<213> ORGANISM: Homo sapiens
```

-continued

```
<400> SEQUENCE: 18
cccagatctc tagaggattc ccctgttcca c                                    31
```

MAGE-A3 PEPTIDES PRESENTED BY HLA CLASS II MOLECULES

RELATED APPLICATIONS

This application is a divisional of U.S. application Ser. No. 09/860,840, filed May 18, 2001, now pending, which is herein incorporated by reference in its entirety.

FIELD OF THE INVENTION

This invention relates to fragments of the tumor associated gene product MAGE-A3 which bind to and are presented to T lymphocytes by HLA class II molecules. The peptides, nucleic acid molecules which code for such peptides, as well as related antibodies and CD4+ T lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response, which in part comprises mature T lymphocytes which are positive for either CD4 or CD8 cell surface proteins. T cells can recognize and interact with other cells via cell surface complexes on the other cells of peptides and molecules referred to as human leukocyte antigens ("HLAs") or major histocompatibility complexes ("MHCs"). The peptides are derived from larger molecules which are processed by the cells which also present the HLA/MHC molecule. See Male et al., *Advanced Immunology* (J.P. Lipincott Company, 1987), especially chapters 6-10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanisms described above are involved in the immune system's response to foreign materials, in autoimmune pathologies, and in responses to cellular abnormalities.

The T cell response to foreign antigens includes both cytolytic T lymphocytes and helper T lymphocytes. CD8+ cytotoxic or cytolytic T cells (CTLs) are T cells which, when activated, lyse cells that present the appropriate antigen presented by HLA class I molecules. CD4+ T helper cells are T cells which secrete cytokines to stimulate macrophages and antigen-producing B cells which present the appropriate antigen by HLA class II molecules on their surface.

The mechanism by which T cells recognize alien materials also has been implicated in cancer. A number of cytolytic T lymphocyte (CTL) clones directed against autologous melanoma have been described. In some instances, the antigens recognized by these clones have been characterized. In De Plaen et al., *Immunogenetics* 40:360-369 (1994), the "MAGE" family, a family of genes encoding tumor specific antigens, is described. (See also PCT application PCT/US92/04354, published on Nov. 26, 1992.) The expression products of these genes are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics* 35: 145 (1992); van der Bruggen et al., *Science* 254: 1643 (1991), for further information on this family of genes. Also, see U.S. Pat. No. 5,342,774.

In U.S. Pat. No. 5,405,940, MAGE nonapeptides are taught which are presented by the HLA-A1 molecule. Given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,591,430, additional isolated MAGE-A3 peptides are taught which are presented by the HLA-A2 molecule. Therefore, a given TRAP can yield a plurality of TRAs.

The foregoing references describe isolation and/or characterization of tumor rejection antigens which are presented by HLA class I molecules. These TRAs can induce activation and proliferation of CD8+ cytotoxic T lymphocytes (CTLs) which recognize tumor cells that express the tumor associated genes (e.g. MAGE genes) which encode the TRAs.

The importance of CD4+ T lymphocytes (helper T cells) in antitumor immunity has been demonstrated in animal models in which these cells not only serve cooperative and effector functions, but are also critical in maintaining immune memory (reviewed by Topalian, *Curr. Opin. Immunol.* 6:741-745, 1994). Moreover, several studies support the contention that poor tumor-specific immunity is due to inadequate activation of T helper cells.

It has recently been demonstrated that the tyrosinase gene encodes peptides which are presented by HLA class II molecules to stimulate CD4+ T lymphocytes (Topalian et al., 1994; Yee et al., *J. Immunol.* 157:4079-4086, 1996; Topalian et al., *J. Exp. Med.* 183:1965-1971, 1996). As with many cancer associated antigens, tyrosinase is expressed in a limited percentage of tumors and in limited types of tumors. Furthermore, the two identified MHC class II binding tyrosinase peptides are HLA-DRB1*0401-restricted peptides, recognized only by cells which express the particular HLA molecule.

More recently, HLA class II peptide have been identified in the MAGE-A3, a cancer-testis antigen widely expressed in cancer cells but not in normal cells except testis. See U.S. Pat. No. 5,965,535 and PCT/US99/21230.

Although the cancer antigens tyrosinase and MAGE-A3 have been shown to contain HLA class II binding peptides, there exist many patients who would not benefit from any therapy which includes helper T cell stimulation via the aforementioned tyrosinase and MAGE-A3 peptides, either because the patient's tumor does not express tyrosinase, or because the patient does not express the appropriate HLA molecule. Accordingly, there is a need for the identification of additional tumor associated antigens which contain epitopes presented by MHC class II molecules and recognized by CD4+ lymphocytes.

SUMMARY OF THE INVENTION

It now has been discovered that the MAGE-A3 gene encodes additional HLA class II binding peptides that are epitopes presented by HLA-DR1. These peptides, when presented by an antigen presenting cell having the appropriate HLA class II molecule, effectively induce the activation and proliferation of CD4+ T lymphocytes.

The invention provides isolated MAGE-A3 peptides which bind HLA class II molecules, and functional variants of such peptides, the functional variants comprising one or more amino acid additions, substitutions or deletions to the MAGE-A3 peptide sequence. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits and vaccine compositions containing the foregoing molecules additionally are provided. The foregoing can be used in the diagnosis or treatment of conditions characterized by the expression of MAGE-A3. As it is known that the members of the MAGE family of polypeptides and nucleic acids share significant sequence identity and functional homology (e.g., as tumor antigens and precursors), the invention also embraces HLA binding peptides of similar amino acid sequence derived from members of the MAGE family other than MAGE-A3. Therefore, it is understood that the disclosure contained herein of MAGE-A3 HLA class II binding peptides, compositions containing such peptides, and methods of identifying and using such peptides applies also to other members of the MAGE tumor associated antigen family.

According to one aspect of the invention, isolated MAGE-A3 HLA class II-binding peptides are provided. The peptides include an amino acid sequence selected from the group consisting of SEQ ID NO:3, SEQ ID NO:4 and SEQ ID NO:7, or a functional variant thereof comprising 1-10 amino acid additions, substitutions or deletions. However, the isolated MAGE-A3 HLA class II binding peptide does not include the full length MAGE-A3 protein sequence, e.g., the amino acid sequence of SEQ ID NO:2.

In certain embodiments, the isolated HLA class II-binding peptides consist essentially of an amino acid sequence selected from the group consisting of SEQ ID NO:3, SEQ ID NO:4 and SEQ ID NO:7, or consist of an amino acid sequence selected from the group consisting of SEQ ID NO:3, SEQ ID NO:4, SEQ ID NO:7 and SEQ ID NO:16. In preferred embodiments, the isolated HLA class II-binding peptide consists of the amino acid sequence set forth as SEQ ID NO:4.

In other embodiments, the isolated MAGE-A3 HLA class II-binding peptides include an endosomal targeting signal, which preferably is an endosomal targeting portion of human invariant chain Ii. In still other embodiments, the isolated MAGE-A3 HLA class II-binding peptides are non-hydrolyzable. Preferred non-hydrolyzable peptides include peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene) amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

According to another aspect of the invention, compositions comprising one or more isolated HLA class I-binding peptides and one or more isolated MAGE-A3 HLA class II-binding peptides are provided. In these compositions, at least one of the isolated MAGE-A3 HLA class II-binding peptides includes an amino acid sequence selected from the group consisting of SEQ ID NO:3, SEQ ID NO:4 and SEQ ID NO:7, or a functional variant thereof. The HLA class II binding peptide does not include a full length MAGE-A3 protein.

In some embodiments, the HLA class I-binding peptides and the MAGE-A3 HLA class II-binding peptides are combined as a polytope polypeptide, e.g., a series of contiguous epitope amino acid sequences, optionally connected by linker (non-epitope) amino acid sequences. Preferably the isolated MAGE-A3 HLA class II-binding peptides consist essentially of an amino acid sequence selected from the group consisting of SEQ ID NO:3, SEQ ID NO:4 and SEQ ID NO:7. In other preferred embodiments, the isolated MAGE-A3 HLA class II-binding peptided consist of an amino acid sequence selected from the group consisting of SEQ ID NO:3, SEQ ID NO:4, SEQ ID NO:7 and SEQ ID NO:16. Most preferably, the isolated MAGE-A3 HLA class II-binding peptide consists of the amino acid sequence set forth as SEQ ID NO:4.

In certain embodiments, the isolated MAGE-A3 HLA class II-binding peptides include an endosomal targeting signal, which preferably includes an endosomal targeting portion of human invariant chain Ii.

According to still another aspect of the invention, compositions are provided, which include one or more of the foregoing isolated MAGE-A3 HLA class II-binding peptides complexed with one or more isolated HLA class II molecules. In certain embodiments, the number of isolated MAGE-A3 HLA class II-binding peptides and the number of isolated HLA class II molecules are equal. Preferably the isolated MAGE-A3 HLA class II-binding peptides and the isolated MAGE-A3 HLA class II molecules are coupled as a tetrameric molecule of individual isolated MAGE-A3 HLA class II-binding peptides bound to individual isolated HLA class II molecules. In the foregoing embodiments, the HLA class II molecules preferably are DR1 molecules.

According to a further aspect of the invention, isolated nucleic acids are provided that encode one or more of the foregoing MAGE-A3 HLA class II-binding peptides. The nucleic acid molecules do not encode full length MAGE-A3 protein. In preferred embodiments the nucleic acids comprise a nucleotide sequence selected from the group consisting of SEQ ID NO:5, SEQ ID NO:6 and SEQ ID NO:15.

Expression vectors that include the foregoing isolated nucleic acids operably linked to a promoter also are provided in accordance with the invention. In the expression vectors, the nucleic acid preferably includes a nucleotide sequence set forth as SEQ ID NO:5, SEQ ID NO:6 or SEQ ID NO:15. Optionally the expression vectors include a nucleic acid which encodes an HLA-DR1 molecule.

According to a further aspect of the invention, host cells are provided that are transfected or transformed with one or more of the foregoing expression vectors. Some of the host cells express HLA-DR1 molecules.

According to yet another aspect of the invention, methods for enriching selectively a population of T lymphocytes with CD4+ T lymphocytes specific for a MAGE-A3 HLA class II-binding peptide are provided. The methods include contacting an isolated population of T lymphocytes with an agent presenting a complex of the MAGE-A3 HLA class II-binding peptide and an HLA class II molecule in an amount sufficient to selectively enrich the isolated population of T lymphocytes with the CD4+ T lymphocytes. The MAGE-A3 HLA class II-binding peptide comprises an amino acid sequence selected from the group consisting of SEQ ID NO:3, SEQ ID NO:4 and SEQ ID NO:7, or a functional variant thereof.

In certain embodiments, the MAGE-A3 HLA class II-binding peptides consist essentially of an amino acid sequence selected from the group consisting of SEQ ID NO:3, SEQ ID NO:4 and SEQ ID NO:7. In other embodiments, the MAGE-A3 HLA class II-binding peptides consist of an amino acid sequence selected from the group consisting of SEQ ID NO:3, SEQ ID NO:4, SEQ ID NO:7 and SEQ ID NO:16. Preferably, the MAGE-A3 HLA class II-binding peptide consists of the amino acid sequence set forth as SEQ ID NO:4. In still other embodiments, the HLA class II molecule is an HLA-DR1 molecule. The MAGE-A3 HLA class II binding peptide can include an endosomal targeting portion of human invariant chain Ii.

According to another aspect of the invention, methods for diagnosing a disorder characterized by expression of MAGE-A3 are provided. The methods include contacting a biological sample isolated from a subject with an agent that is specific for the MAGE-A3 HLA class II binding peptide, and determining the interaction between the agent and the MAGE-A3 HLA class II binding peptide as a determination of the disorder. In these methods, the MAGE-A3 HLA class II-binding peptide comprises an amino acid sequence selected from the group consisting of SEQ ID NO:3, SEQ ID NO:4 and SEQ ID NO:7, or a functional variant thereof. In preferred methods, the MAGE-A3 HLA class II-binding peptide consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. Preferably, the MAGE-A3 HLA class II-binding peptide consists of the amino acid sequence set forth as SEQ ID NO:4. In the foregoing methods, the agent preferably is an antibody or an antigen binding fragment thereof.

An additional aspect of the invention provides methods for diagnosing a disorder characterized by expression of a MAGE-A3 HLA class II-binding peptide, which forms a complex with an HLA class II molecule. The methods include contacting a biological sample isolated from a subject with an agent that binds the complex and determining binding between the complex and the agent as a determination of the disorder. In such methods the HLA class II molecule is an HLA-DR1 and the MAGE-A3 HLA class II-binding peptide comprises an amino acid sequence selected from the group consisting of SEQ ID NO:3, SEQ ID NO:4 and SEQ ID NO:7, or a functional variant thereof.

In some embodiments, the MAGE-A3 HLA class II-binding peptide consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. In preferred embodiments, the MAGE-A3 HLA class II-binding peptide consists of the amino acid sequence set forth as SEQ ID NO:4.

A further aspect of the invention provides methods for treating a subject having a disorder characterized by expression of MAGE-A3. The methods include administering to the subject an amount of a MAGE-A3 HLA class II-binding peptide effective to ameliorate the disorder, wherein the MAGE-A3 HLA class II-binding peptide comprises an amino acid sequence selected from the group consisting of SEQ ID NO:3, SEQ ID NO:4 and SEQ ID NO:7, or a functional variant thereof.

In some embodiments, the MAGE-A3 HLA class II binding peptide comprises an endosomal targeting signal, preferably an endosomal targeting portion of human invariant chain Ii. In other embodiments, the MAGE-A3 HLA class II-binding peptide consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. Preferably, the MAGE-A3 HLA class II-binding peptide consists of the amino acid sequence set forth as SEQ ID NO:4.

According to another aspect of the invention, methods for treating a subject having a disorder characterized by expression of MAGE-A3 are provided. The methods include administering to the subject an amount of a HLA class I-binding peptide and an amount of a MAGE-A3 HLA class II-binding peptide effective to ameliorate the disorder. In these methods, the MAGE-A3 HLA class II-binding peptide comprises an amino acid sequence selected from the group consisting of SEQ ID NO:3, SEQ ID NO:4 and SEQ ID NO:7, or a functional variant thereof.

In some embodiments the HLA class I-binding peptide and the MAGE-A3 HLA class II-binding peptide are combined as a polytope polypeptide. In other embodiments, the HLA class I-binding peptide is a MAGE-A3 HLA class I-binding peptide. In still other embodiments, the MAGE-A3 HLA class II binding peptide comprises an endosomal targeting signal, preferably an endosomal targeting portion of human invariant chain Ii.

The MAGE-A3 HLA class II-binding peptide, in certain embodiments consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. Preferably the MAGE-A3 HLA class II-binding peptide consists of the amino acid sequence set forth as SEQ ID NO:4.

According to still another aspect of the invention, additional methods for treating a subject having a disorder characterized by expression of MAGE-A3 are provided. The methods include administering to the subject an amount of an agent which enriches selectively in the subject the presence of complexes of an HLA class II molecule and a MAGE-A3 HLA class II-binding peptide, sufficient to ameliorate the disorder. In these methods, the HLA class II molecule is an HLA-DR1 molecule and the MAGE-A3 HLA class II-binding peptide comprises an amino acid sequence selected from the group consisting of SEQ ID NO:3, SEQ ID NO:4 and SEQ ID NO:7, or a functional variant thereof.

In certain embodiments, the MAGE-A3 HLA class II-binding peptide consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. Preferably, the MAGE-A3 HLA class II-binding peptide consists of the amino acid sequence set forth as SEQ ID NO:4.

In other embodiments, the agent comprises a MAGE-A3 HLA class II binding peptide. Preferably the MAGE-A3 HLA class II binding peptide comprises an endosomal targeting signal. More preferably the endosomal targeting signal comprises an endosomal targeting portion of human invariant chain Ii.

In another aspect of the invention, other methods for treating a subject having a disorder characterized by expression of MAGE-A3 are provided. The methods include administering to the subject an amount of autologous CD4+ T lymphocytes sufficient to ameliorate the disorder, wherein the CD4+ T lymphocytes are specific for complexes of an HLA class II molecule and a MAGE-A3 HLA class II-binding peptide. In such methods the HLA class II molecule is an HLA-DR1 molecule and the MAGE-A3 HLA class II-binding peptide comprises an amino acid sequence selected from the group consisting of SEQ ID NO:3, SEQ ID NO:4 and SEQ ID NO:7, or a functional variant thereof.

In certain embodiments of these methods the MAGE-A3 HLA class II-binding peptide consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. Preferably the MAGE-A3 HLA class II-binding peptide consists of the amino acid sequence set forth as SEQ ID NO:4.

Methods for identifying functional variants of a MAGE-A3 HLA class II binding peptide are also provided in another aspect of the invention. The methods include selecting a MAGE-A3 HLA class II binding peptide which comprises an amino acid sequence selected from the group consisting of SEQ ID NO:3, SEQ ID NO:4 and SEQ ID NO:7, an HLA class II binding molecule which binds the MAGE-A3 HLA class II binding peptide, and a T cell which is stimulated by the MAGE-A3 HLA class II binding peptide presented by the HLA class II binding molecule. The methods also include mutating a first amino acid residue of the MAGE-A3 HLA class II binding peptide to prepare a variant peptide and determining the binding of the variant peptide to HLA class II binding molecule and the stimulation of the T cell. Binding of the variant peptide to the HLA class II binding molecule and stimulation of the T cell by the variant peptide presented by the HLA class II binding molecule indicates that the variant peptide is a functional variant.

In some embodiments, the foregoing methods also include a step of comparing the stimulation of the T cell by the MAGE-A3 HLA class II binding peptide and the stimulation of the T cell by the functional variant as a determination of the effectiveness of the stimulation of the T cell by the functional variant.

In another aspect of the invention, isolated polypeptides are provided which binds selectively an isolated MAGE-A3 HLA class II-binding peptide that consists essentially of an amino acid sequence selected from the group consisting of SEQ ID NO:3, SEQ ID NO:4 and SEQ ID NO:7, provided that the isolated polypeptide is not an HLA class II molecule.

In certain embodiments, the isolated polypeptide is an antibody, preferably a monoclonal antibody. Preferred monoclonal antibodies include human antibodies, humanized antibodies, chimeric antibodies and single chain antibodies. In other embodiments, the isolated polypeptide is an antibody fragment. Preferred antibody fragments include Fab fragments, F(ab)$_2$ fragments, Fv fragments and fragments including a CDR3 region selective for a MAGE-A3 HLA class II-binding peptide.

In another aspect of the invention, isolated CD4+ T lymphocytes which selectively bind a complex of an HLA class II molecule and a MAGE-A3 HLA class II-binding peptide are provided. The HLA class II molecule is an HLA-DR1 molecule and wherein the MAGE-A3 HLA class II-binding peptide comprises an amino acid sequence selected from the group consisting of SEQ ID NO:3, SEQ ID NO:4 and SEQ ID NO:7, or a functional variant thereof. In certain embodiments, the MAGE-A3 HLA class II-binding peptide consists essentially of an amino acid sequence selected from the group consisting of SEQ ID NO:3, SEQ ID NO:4 and SEQ ID NO:7, or consists of an amino acid sequence selected from the group consisting of SEQ ID NO:3, SEQ ID NO:4, SEQ ID NO:7 and SEQ ID NO:16. Preferably the MAGE-A3 HLA class II-binding peptide consists of the amino acid sequence set forth as SEQ ID NO:4.

According to yet another aspect of the invention, isolated antigen presenting cells are provided which include a complex of an HLA class II molecule and a MAGE-A3 HLA class II-binding peptide. In these cells the HLA class II molecule is an HLA-DR1 molecule and the MAGE-A3 HLA class II-binding peptide includes an amino acid sequence selected from the group consisting of SEQ ID NO:3, SEQ ID NO:4 and SEQ ID NO:7. In some embodiments, the MAGE-A3 HLA class II-binding peptide consists essentially of an amino acid sequence selected from the group consisting of SEQ ID NO:3, SEQ ID NO:4 and SEQ ID NO:7 or consists of an amino acid sequence selected from the group consisting of SEQ ID NO:3, SEQ ID NO: 4, SEQ ID NO:7 and SEQ ID NO:16. Preferably the MAGE-A3 HLA class II-binding peptide consists of the amino acid sequence set forth as SEQ ID NO:4.

The invention also provides pharmaceutical preparations containing any one or more of the medicaments described above or throughout the specification. Such pharmaceutical preparations can include pharmaceutically acceptable diluent carriers or excipients.

The use of the foregoing compositions, peptides and nucleic acids in the preparation of a medicament, particularly a medicament for treatment of cancer, also is provided.

These and other objects of the invention will be described in further detail in connection with the detailed description of the invention.

BRIEF DESCRIPTION OF THE DRAWINGS

FIG. 2 is a graph showing titration of the MAGE-A3 peptide recognized by CD4+ clone MAGJ569/F4.3. In FIG. 2A, the following peptides were tested: GSDPACYEFLWGPRAL (MAGE-A3$_{263-278}$; SEQ ID NO:3), ACYEFLWGPRALVETS (MAGE-A3$_{267-282}$; SEQ ID NO:4), ACYEFLWGPRALVE (SEQ ID NO:7), ACYEFLWGPRALV (SEQ ID NO:8), ACYEFLWGPRAL (SEQ ID NO:9), ACYEFLWGPRA (SEQ ID NO:10), ACYEFLWGPR (SEQ ID NO:11), CYEFLWGPRALVE (SEQ ID NO:12), YEFLWGPRALVE (SEQ ID NO:13) and EFLWGPRALVE (SEQ ID NO:14). In FIG. 2B, the following peptides were tested: GSDPACYEFLWGPRAL (SEQ ID NO:3), ACYEFLWGPRALVETS (SEQ ID NO:4), ACYEFLWGPRALVE (SEQ ID NO:7) and ACYEFLWGPRALV (SEQ ID NO:8).

DETAILED DESCRIPTION OF THE INVENTION

Figure 1:
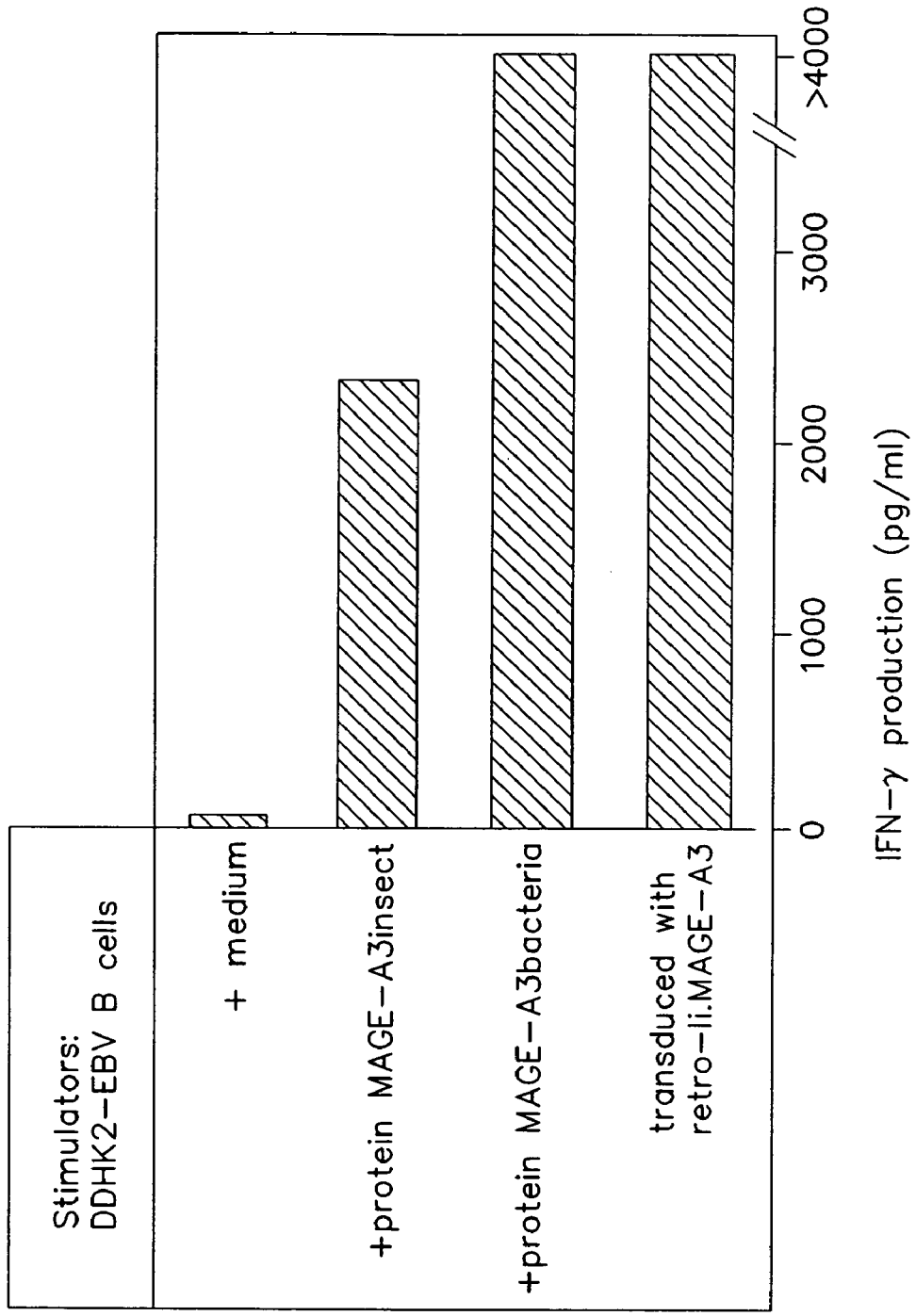
FIG. 1 shows that a CD4+ T cell clone directed against a MAGE-A3 derived antigen.

The invention provides isolated MAGE-A3 peptides presented by HLA class II molecules, which peptides stimulate the proliferation and activation of CD4⁺ T lymphocytes. Such peptides are referred to herein as "MAGE-A3 HLA class II binding peptides," "HLA class II binding peptides" and "MHC class II binding peptides." Hence, one aspect of the invention is an isolated peptide which includes the amino acid sequence of SEQ ID NO:4. The peptides referred to herein as "MAGE-A3 HLA class II binding peptides" include fragments of MAGE-A3 protein, but do not include full-length MAGE-A3 protein. Likewise, nucleic acids that encode the "MAGE-A3 HLA class II binding peptides" include fragments of the MAGE-A3 gene coding region, but do not include the full-length MAGE-A3 coding region.

The examples below show the isolation of peptides which are MAGE-A3 HLA class II binding peptides. These exemplary peptides are processed translation products of the MAGE-A3 nucleic acid (SEQ ID NO:1, the polypeptide sequence of which is given as SEQ ID NO:2). As such, it will be appreciated by one of ordinary skill in the art that the translation products from which a MAGE-A3 HLA class II binding peptide is processed to a final form for presentation may be of any length or sequence so long as they encompass the MAGE-A3 HLA class II binding peptide. As demonstrated in the examples below, peptides or proteins as small as 13 or 14 amino acids and as large as the amino acid sequence of the MAGE-A3 protein (SEQ ID NO:2) are appropriately processed, presented by HLA class II molecules and effective in stimulating CD4⁺ T lymphocytes. MAGE-A3 HLA class II binding peptides, such as the peptides of SEQ ID NO:3, SEQ ID NO:4 or SEQ ID NO:7 may have one, two, three, four, five, six, seven, eight, nine, ten, 15, 20, 25, 30, 40, 50 or more amino acids added to either or both ends. The antigenic portion of such a peptide is cleaved out under physiological conditions for presentation by HLA class II molecules. It is also well known in the art that HLA class II peptide length is variable between about 10 amino acids and about 30 amino acids (Engelhard, *Ann. Rev. Immunol.* 12:181-201, 1994). Most of the HLA class II binding peptides fall in to the length range of 12-19 amino acids. Nested sets of HLA class II binding peptides have been identified, wherein the peptides share a core sequence but have different amino acids at amino and/or carboxyl terminal ends (see, e.g., Chicz et al., *J. Exp. Med.* 178:27-47, 1993). Thus additional MAGE-A3 HLA class II binding peptides, as well as MAGE family HLA class II binding peptides, can be identified by one of ordinary skill in the art according to the procedures described herein.

The procedures described in the Examples can be utilized to identify MAGE family HLA class II binding peptides. Thus, for example, one can load antigen presenting cells, such as dendritic cells of normal blood donors, with a recombinant MAGE protein (or a fragment thereof) by contacting the cells with the MAGE polypeptide or by introducing into the cells a nucleic acid molecule which directs the expression of the MAGE protein of interest. The antigen-presenting cells then can be used to induce in vitro the activation and proliferation of specific CD4 lymphocytes which recognize MAGE HLA class II binding peptides. The sequence of the peptides then can be determined as described in the Examples, e.g., by stimulating cells with peptide fragments of the MAGE protein used to stimulate the activation and proliferation of CD4 lymphocytes. Alternatively, one can load antigen presenting cells with peptides derived from a MAGE protein. For example, one can make predictions of peptide sequences derived from MAGE family proteins which are candidate HLA class II binding peptides based on the consensus amino acid sequences for binding HLA class II molecules. In this regard, see, e.g. International applications PCT/US96/03182 and PCT/US98/01373. Peptides which are thus selected can be used in the assays described herein for inducing specific CD4 lymphocytes and identification of peptides. Additional methods of selecting and testing peptides for HLA class II binding are well known in the art.

As noted above, the invention embraces functional variants of MAGE-A3 HLA class II binding peptides. As used herein, a "functional variant" or "variant" of a HLA class II binding peptide is a peptide which contains one or more modifications to the primary amino acid sequence of a HLA class II binding peptide and retains the HLA class II and T cell receptor binding properties disclosed herein. Modifications which create a MAGE-A3 HLA class II binding peptide functional variant can be made for example 1) to enhance a property of a MAGE-A3 HLA class II binding peptide, such as peptide stability in an expression system or the stability of protein-protein binding such as HLA-peptide binding; 2) to provide a novel activity or property to a MAGE-A3 HLA class II binding peptide, such as addition of an antigenic epitope or addition of a detectable moiety; or 3) to provide a different amino acid sequence that produces the same or similar T cell stimulatory properties. Modifications to MAGE-A3 (as well as MAGE family) HLA class II binding peptides can be made to nucleic acids which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Variants also can be selected from libraries of peptides, which can be random peptides or peptides based on the sequence of the MAGE peptides including substitutions at one or more positions. For example, a peptide library can be used in competition assays with complexes of MAGE peptides bound to HLA class II molecules (e.g. dendritic cells loaded with MAGE peptide). Peptides which compete for binding of the MAGE peptide to the HLA class II molecule can be sequenced and used in other assays (e.g. CD4 lymphocyte proliferation) to determine suitability as MAGE peptide functional variants.

Modifications also embrace fusion proteins comprising all or part of a MAGE HLA class II binding peptide amino acid sequence, such as the invariant chain-MAGE-A3 fusion proteins described herein. The invention thus embraces fusion proteins comprising MAGE-A3 HLA class II binding peptides and endosomal targeting signals such as the human invariant chain (Ii). As is disclosed below, fusion of an endosomal targeting portion of the human invariant chain to MAGE-A3 resulted in efficient targeting of MAGE-A3 to the HLA class II peptide presentation pathway. An "endosomal targeting portion" of the human invariant chain or other targeting polypeptide is that portion of the molecule which, when fused or conjugated to a second polypeptide, increases endosomal localization of the second polypeptide. Thus endosomal targeting portions can include the entire sequence or only a small portion of a targeting polypeptide such as human invariant chain Ii. One of ordinary skill in the art can readily determine an endosomal targeting portion of a targeting molecule.

Prior investigations (PCT/US99/21230) noted that fusion of an endosomal targeting portion of LAMP-1 protein did not significantly increase targeting of MAGE-A3 to the HLA class II peptide presentation pathway. Therefore, the particular MAGE-A3 peptides of the invention can be tested as fusions with LAMP-1 to determine if such fusion proteins are efficiently targeted to the HLA class II peptide presentation pathway. Additional endosomal targeting signals can be identified by one of ordinary skill in the art, fused to MAGE-A3 or a MAGE-A3 HLA class II binding portion thereof, and tested for targeting to the HLA class II peptide presentation pathway using no more than routine experimentation.

The amino acid sequence of MAGE HLA class II binding peptides may be of natural or non-natural origin, that is, they may comprise a natural MAGE HLA class II binding peptide molecule or may comprise a modified sequence as long as the amino acid sequence retains the ability to stimulate helper T cells when presented and retains the property of binding to an HLA class II molecule such as an HLA DR1 molecule. For example, MAGE-A3 HLA class II binding peptides in this context may be fusion proteins including a MAGE-A3 HLA class II binding peptide and unrelated amino acid sequences, synthetic MAGE-A3 HLA class II binding peptides, labeled peptides, peptides isolated from patients with a MAGE-A3 expressing cancer, peptides isolated from cultured cells which express MAGE-A3, peptides coupled to nonpeptide molecules (for example in certain drug delivery systems) and other molecules which include the amino acid sequence of SEQ ID NO:3, SEQ ID NO:4 or SEQ ID NO:7.

Preferably, the MAGE-A3 HLA class II binding peptides are non-hydrolyzable. To provide such peptides, one may select MAGE-A3 HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing CD4+ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a MAGE-A3 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include, but are not limited to, -psi[CH$_2$NH]-reduced amide peptide bonds, -psi[COCH$_2$]-ketomethylene peptide bonds, -psi[CH(CN)NH]-(cyanomethylene)amino peptide bonds, -psi [CH$_2$CH(OH)]-hydroxyethylene peptide bonds, -psi[CH$_2$O]-peptide bonds, and -psi[CH$_2$S]-thiomethylene peptide bonds.

Nonpeptide analogs of peptides, e.g., those which provide a stabilized structure or lessened biodegradation, are also contemplated. Peptide mimetic analogs can be prepared based on a selected MAGE-A3 HLA class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., *Regul. Pept.* 57:359-370 (1995). Peptide as used herein embraces all of the foregoing.

If a variant involves a change to an amino acid of SEQ ID NO:3, SEQ ID NO:4, or SEQ ID NO:7, functional variants of the MAGE-A3 HLA class II binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the MAGE-A3 HLA class II binding peptides are provided in a published PCT application of Strominger and Wucherpfennig (PCT/US96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Other computational methods for selecting amino acid substitutions, such as iterative computer structural modeling, can also be performed by one of ordinary skill in the art to prepare variants. Sequence motifs for MAGE-A3 HLA class II binding peptide functional variants can be developed by analysis of the binding domains or binding pockets of major histocompatibility complex HLA-DR proteins and/or the T cell receptor ("TCR") contact points of the MAGE-A3 HLA class II binding peptides disclosed herein. By providing a detailed structural analysis of the residues involved in forming the HLA class II binding pockets, one is enabled to make predictions of sequence motifs for binding of MAGE peptides to any of the HLA class II proteins.

Using these sequence motifs as search, evaluation, or design criteria, one is enabled to identify classes of peptides (e.g. MAGE HLA class II binding peptides, particularly the MAGE-A3 peptides disclosed herein, and functional variants thereof) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. By keeping the residues which are likely to bind in the HLA class II and/or TCR binding pockets constant or permitting only specified substitutions, functional variants of MAGE HLA class II binding peptides can be prepared which retain binding to HLA class II and T cell receptor.

Thus methods for identifying additional MAGE family HLA class II peptides, in particular MAGE-A3 HLA class II binding peptides, and functional variants thereof, are provided. In general, any MAGE protein can be subjected to the analysis noted above, peptide sequences selected and the tested as described herein. With respect to MAGE-A3, for example, the methods include selecting a MAGE-A3 HLA class II binding peptide, an HLA class II binding molecule which binds the MAGE-A3 HLA class II binding peptide, and a T cell which is stimulated by the MAGE-A3 HLA class II binding peptide presented by the HLA class II binding molecule. In preferred embodiments, the MAGE-A3 HLA class II binding peptide comprises the amino acid sequence of SEQ ID NO:3, SEQ ID NO:4 or SEQ ID NO:7. More preferably, the peptide consists essentially of those amino acid sequences. A first amino acid residue of the MAGE-A3 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecule and stimulation of the T cell are then determined according to standard procedures. For example, as exemplified below, the variant peptide can be contacted with an antigen presenting cell which contains the HLA class II molecule which binds the MAGE-A3 peptide to form a complex of the variant peptide and antigen presenting cell. This complex can then be contacted with a T cell which recognizes the MAGE-A3 HLA class II binding peptide presented by the HLA class II binding molecule. T cells can be obtained from a patient having a condition characterized by expression of MAGE-A3, such as cancer. Recognition of variant peptides by the T cells can be determined by measuring an indicator of T cell stimulation such as TNF or IFNγ production. Similar procedures can be carried out for identification and characterization of other MAGE family HLA class II binding peptides.

Binding of a variant peptide to the HLA class II binding molecule and stimulation of the T cell by the variant peptide presented by the HLA class II binding molecule indicates that the variant peptide is a functional variant. The methods also can include the step of comparing the stimulation of the T cell by the MAGE-A3 HLA class II binding peptide and the stimulation of the T cell by the functional variant as a determination of the effectiveness of the stimulation of the T cell by the functional variant. By comparing the functional variant with the MAGE-A3 HLA class II binding peptide, peptides with increased T cell stimulatory proterties can be prepared.

The forgoing methods can be repeated sequentially with a second, third, fourth, fifth, sixth, seventh, eighth, ninth, and tenth substitutions to prepare additional functional variants of the disclosed MAGE-A3 HLA class II binding peptides.

Variants of the MAGE-A3 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a MAGE HLA class II binding peptides or variants thereof and other nucleic acid sequences which hybridize to a nucleic acid molecule consisting of the above described nucleotide sequences, under stringent conditions. Preferred nucleic acid molecules include those comprising the nucleotide sequences that encode SEQ ID NOs:3, 4 and 7, which are SEQ ID NOs:5, 6 and 15, respectively. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15M Sodium Chloride/0.15M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1× SDS at temperatures up to 68° C. Alternatively, stringent hybridization may be performed using a commercially available hybridization buffer, such as ExpressHyb™ buffer (Clontech) using hybridization and washing conditions described by the manufacturer.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the MAGE HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 90% amino acid identity and/or at least 75% nucleotide identity to the amino acid sequence of a MAGE-A3 HLA class II binding peptide (such as SEQ ID NO:3, SEQ ID NO:4 and SEQ ID NO:7) or nucleic acids which encode such a peptide, respectively. In some instances homologs and alleles will share at least 90% nucleotide identity and/or at least 95% amino acid identity and in still other instances will share at least 95% nucleotide identity and/or at least 99% amino acid identity. Complements of the foregoing nucleic acids also are embraced by the invention.

In screening for nucleic acids which encode a MAGE HLA class II binding peptide, a nucleic acid hybridization such as a Southern blot or a Northern blot may be performed using the foregoing conditions, together with a detectably labeled probe (e.g., radioactive such as $^{32}P$, chemiluminescent, fluorescent labels). After washing the membrane to which DNA encoding a MAGE HLA class II binding peptide was finally transferred, the membrane can be placed against X-ray film, phosphorimager or other detection device to detect the detectable label.

The invention also includes the use of nucleic acid sequences which include alternative codons that encode the same amino acid residues of the MAGE HLA class II binding peptides. For example, as disclosed herein, the peptide ACYEFLWGPRALVETS (SEQ ID NO:4) is a MAGE-A3 HLA class II binding peptide. The leucine residues (amino acids No. 6 and 12 of SEQ ID NO:4) can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the MAGE-A3 HLA class II binding peptide of SEQ ID NO:4 include: CGA, CGC, CGG, CGT, AGA and AGG (arginine codons); GUA, GUC, GUG and GUU (valine codons); GAA and GAG (glutamine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native MAGE HLA class II binding peptide encoding nucleic acids in codon sequence due to the degeneracy of the genetic code.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DR1 molecules present a MAGE-A3 HLA class II binding peptide, the expression vector may also include a nucleic acid sequence coding for an HLA-DR1 molecule. In a situation where the vector contains both coding sequences, it can be used to transfect a cell which does not normally express either one. The MAGE-A3 HLA class II binding peptide coding sequence may be used alone, when, e.g. the host cell already expresses an HLA-DR1 molecule. Of course, there is no limit on the particular host cell which can be used as the vectors which contain the two coding sequences may be used in host cells which do not express HLA-DR1 molecules if desired, and the nucleic acid coding for the MAGE-A3 HLA class II binding peptide can be used in antigen presenting cells which express an HLA-DR1 molecule.

As used herein, "an HLA-DR1 molecule" includes the subtypes DRB1*0101, DRB1*01021, DRB1*01022, DRB1*0103, DRB1*0104, DRB1*0105, DRB1*0106, DRB1*0107 and other subtypes known to one of ordinary skill in the art. Other subtypes can be found in various publications that update HLA allele lists.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis.

In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target a MAGE family polypeptide, e.g. MAGE-A3, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore it is preferable that the MAGE-A3 HLA class II binding peptides and precursors thereof (e.g. the MAGE-A3 protein) are targeted to the endosome, thereby enhancing MAGE-A3 HLA class II binding peptide binding to HLA class II molecules. Targeting signals for directing molecules to endosomes are known in the art and these signals conveniently can be incorporated in expression vectors such that fusion proteins which contain the endosomal targeting signal are produced. Sanderson et al. (*Proc. Nat'l. Acad. Sci. USA* 92:7217-7221, 1995), Wu et al. (*Proc. Nat'l. Acad. Sci. USA* 92:11671-11675, 1995) and Thomson et al (*J. Virol.* 72:2246-2252, 1998) describe endosomal targeting signals (including invariant chain Ii and lysosomal-associated membrane protein LAMP-1) and their use in directing antigens to endosomal and/or lysosomal cellular compartments. As disclosed in the Examples, invariant chain-MAGE-A3 fusion proteins are preferred.

Endosomal targeting signals such as invariant chain also can be conjugated to MAGE-A3 protein or peptides by non-peptide bonds (i.e. not fusion proteins) to prepare a conjugate capable of specifically targeting MAGE-A3. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulfhydryls, carboxyls, carbonyls and carbohydrates. One of ordinary skill in the art will be able to ascertain without undue experimentation the preferred molecule for linking the endosomal targeting moiety and MAGE-A3 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a MAGE-A3 HLA class II binding peptide. That heterologous DNA (RNA) is placed under operable control of transcriptional elements to permit the expression of the heterologous DNA in the host cell. As described herein, such expression constucts optionally also contain nucleotide sequences which encode endosomal targeting signals, preferably human invariant chain or a targeting fragment thereof Preferred systems for mRNA expression in mammalian cells are those such as pRc/CMV and pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer*, 67:303-310, 1996). Recombinant vectors including viruses selected from the group consisting of adenoviruses, adeno-associated viruses, poxviruses including vaccinia viruses and attenuated poxviruses such as ALVAC, NYVAC, Semliki Forest virus, Venezuelan equine encephalitis virus, retroviruses, Sindbis virus, Ty virus-like particle, other alphaviruses, VSV, plasmids (e.g. "naked" DNA), bacteria (e.g. the bacterium Bacille Calmette Guerin, attenuated *Salmonella*), and the like can be used in such delivery, for example, for use as a vaccine.

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for MAGE-A3 HLA class II binding peptides but are equally applicable to use of other MAGE family HLA class II binding peptides. First, the invention permits the artisan to diagnose a disorder characterized by expression of a MAGE-A3 HLA class II binding peptide. These methods involve determining expression of a MAGE-A3 HLA class II binding peptide, or a complex of a MAGE-A3 HLA class II binding peptide and an HLA class II molecule in a biological sample. The expression of a peptide or complex of peptide and HLA class II molecule can be determined by assaying with a binding partner for the peptide or complex, such as an antibody.

The invention further includes nucleic acid or protein microarrays with components that bind MAGE-A3 HLA class II peptides or nucleic acids encoding such polypeptides. In this aspect of the invention, standard techniques of microarray technology are utilized to assess expression of the MAGE-A3 polypeptides and/or identify biological constituents that bind such polypeptides. The constituents of biological samples include antibodies, lymphocytes (particularly T lymphocytes), and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485): 1760-1763, 2000. Nucleic acid arrays, particularly arrays that bind MAGE-A3 peptides also can be used for diagnostic applications, such as for identifying subjects that have a condition characterized by MAGE-A3 polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

Targets are peptides or proteins and may be natural or synthetic. The tissue may be obtained from a subject or may be grown in culture (e.g. from a cell line).

In some embodiments of the invention one or more control peptide or protein molecules are attached to the substrate. Preferably, control peptide or protein molecules allow determination of factors such as peptide or protein quality and binding characteristics, reagent quality and effectiveness, binding success, and analysis thresholds and success.

In other embodiments, one or more control peptide or nucleic acid molecules are attached to the substrate. Preferably, control nucleic acid molecules allow determination of factors such as binding characteristics, reagent quality and effectiveness, hybridization success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more molecule that bind the nucleic acid molecules that encode the MAGE-A3 HLA class II binding peptides set forth herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

In some embodiments, one or more control peptide or nucleic acid molecules are attached to the substrate. Preferably, control nucleic acid molecules allow determination of factors such as binding characteristics, reagent quality and effectiveness, hybridization success, and analysis thresholds and success.

The invention also permits the artisan to treat a subject having a disorder characterized by expression of a MAGE-A3 HLA class II binding peptide. Treatments include administering an agent which enriches in the subject a complex of a MAGE-A3 HLA class II binding peptide and an HLA class II molecule, and administering $CD4^+$ T lymphocytes which are specific for such complexes. Agents useful in the foregoing treatments include MAGE-A3 HLA class II binding peptides and functional variants thereof, endosome-targeted fusion proteins which include such MAGE-A3 peptides, nucleic acids which express such proteins and peptides (including viruses which contain the nucleic acids), complexes of such peptides and HLA class II binding molecules (e.g. HLA DR1), antigen presenting cells bearing complexes of a MAGE-A3 HLA class II binding peptide and an HLA class II binding molecule, and the like. The invention also permits an artisan to selectively enrich a population of T lymphocytes for CD4+ T lymphocytes specific for a MAGE-A3 HLA class II binding peptide.

The isolation of the MAGE-A3 HLA class II binding peptides also makes it possible to isolate nucleic acids which encode the MAGE-A3 HLA class II binding peptides. Nucleic acids can be used to produce in vitro or in prokaryotic or eukaryotic host cells the MAGE-A3 HLA class II binding peptides. A variety of methodologies well-known to the skilled practitioner can be utilized to obtain isolated MAGE-A3 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the MAGE-A3 HLA class II binding peptide of the invention may also be synthesized in vitro. Those skilled in the art also can readily follow known methods for isolating peptides in order to obtain isolated MAGE-A3 HLA class II binding peptides. These include, but are not limited to, immunochromatography, HPLC, size-exclusion chromatography, ion-exchange chromatography and immune-affinity chromatography.

These isolated MAGE-A3 HLA class II binding peptides, proteins which include such peptides, or complexes of the peptides and HLA class II molecules, such as HLA-DR1 molecule, may be combined with materials such as adjuvants to produce vaccines useful in treating disorders characterized by expression of the MAGE-A3 HLA class II binding peptide. In addition, vaccines can be prepared from cells which present the MAGE-A3 HLA class II binding peptide/HLA complexes on their surface, such as dendritic cells, B cells, non-proliferative transfectants, et cetera. In all cases where cells are used as a vaccine, these can be cells transfected with coding sequences for one or both of the components necessary to stimulate CD4+ lymphocytes, or be cells which already express both molecules without the need for transfection. For example, autologous antigen presenting cells can be isolated from a patient and treated to obtain cells which present MAGE-A3 epitopes in association of HLA class I and HLA class II molecules. These cells would be capable of stimulating both CD4+ and CD8+ cell responses. Such antigen presenting cells can be obtained by infecting dendritic cells with recombinant viruses encoding an Ii.MAGE-A3 fusion protein. Dendritic cells also can be loaded with HLA class I and HLA class II epitopes.

Vaccines also encompass naked DNA or RNA, encoding a MAGE-A3 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259: 1745-1748, 1993). Vaccines also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a given antigen can be detected by direct labeling of T cell receptors with soluble fluorogenic MHC molecule tetramers which present the antigenic peptide (Altman et al., *Science* 274:94-96, 1996; Dunbar et al., *Curr. Biol.* 8:413-416, 1998). Briefly, soluble MHC class I molecules are folded in vitro in the presence of β2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675-682, 1998). Multimeric soluble MHC class II molecules were complexed with a covalently attached peptide. The class II tetramers were shown to bind with appropriate specificity and affinity to specific T cells. Thus tetramers can be used to monitor both CD4+ and CD8+ cell responses to vaccination protocols.

The MAGE-A3 HLA class II binding peptide, as well as complexes of MAGE-A3 HLA class II binding peptide and HLA molecule, also may be used to produce antibodies, using standard techniques well known to the art. Standard reference works setting forth the general principles of antibody production include Catty, D., *Antibodies, A Practical Approach*, Vol. 1, IRL Press, Washington, D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. See, e.g., U.S. Pat. Nos. 5,545,806, 6,150,584, and references cited therein. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the peptide/HLA complexes described herein.

When "disorder" or "condition" is used herein, it refers to any pathological condition where the MAGE-A3 HLA class II binding peptide is expressed. Such disorders include cancers, such as melanomas, squamous cell carcinomas of the head, neck, lung or esophagus, colorectal carcinomas, osteosarcomas, neuroblastomas, non-squamous cell carcinomas of the head or neck, ovarian tumors, lymphocytic leukemias, bladder carcinomas, prostate carcinomas, etc.

Some therapeutic approaches based upon the disclosure are premised on inducing a response by a subject's immune system to MAGE HLA class II binding peptide presenting cells. One such approach is the administration of autologous CD4$^+$ T cells specific to the complex of MAGE-A3 HLA class II binding peptide and an HLA class II molecule to a subject with abnormal cells of the phenotype at issue. It is within the skill of the artisan to develop such CD4$^+$ T cells in vitro. Generally, a sample of cells taken from a subject, such as blood cells, are contacted with a cell presenting the complex and capable of provoking CD4$^+$ T lymphocytes to proliferate. The target cell can be a transfectant, such as a COS cell, or an antigen presenting cell bearing HLA class II molecules, such as dendritic cells or B cells. These transfectants present the desired complex of their surface and, when combined with a CD4$^+$ T lymphocyte of interest, stimulate its proliferation. COS cells are widely available, as are other suitable host cells. Specific production of CD4$^+$ T lymphocytes is described below. The clonally expanded autologous CD4$^+$ T lymphocytes then are administered to the subject. The CD4$^+$ T lymphocytes then stimulate the subject's immune response, thereby achieving the desired therapeutic goal.

CTL proliferation can be increased by increasing the level of tryptophan in T cell cultures, by inhibiting enzymes which catabolizes tryptophan, such as indoleamine 2,3-dioxygenase (IDO), or by adding tryptophan to the culture (see, e.g., PCT application WO99/29310). Proliferation of T cells is enhanced by increasing the rate of proliferation and/or extending the number of divisions of the T cells in culture. In addition, increasing tryptophan in T cell cultures also enhances the lytic activity of the T cells grown in culture.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a MAGE-A3 sequence.

The foregoing therapy is not the only form of therapy that is available in accordance with the invention. CD4$^+$ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (*Proc. Natl. Acad. Sci. USA* 88: 110-114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a MAGE-A3 HLA class II binding peptide may be operably linked to promoter and enhancer sequences which direct expresion of the MAGE-A3 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding MAGE-A3 HLA class II binding peptides. Nucleic acids encoding a MAGE-A3 HLA class II binding peptide also may be inserted into a retroviral genome, thereby facilitating integration of the nucleic acid into the genome of the target tissue or cell type. In these systems, the gene of interest is carried by a microorganism, e.g., a *Vaccinia* virus, poxviruses in general, adenovirus, herpes simplex virus, retrovirus or the bacteria BCG, and the materials de facto "infect" host cells. The cells which result present the complex of interest, and are recognized by autologous CD4$^+$ T cells, which then proliferate.

A similar effect can be achieved by combining a MAGE HLA class II binding peptide with an adjuvant to facilitate incorporation into HLA class II presenting cells in vivo. If larger than the HLA class II binding portion, the MAGE-A3 HLA class II binding peptide can be processed if necessary to yield the peptide partner of the HLA molecule while the TRA is presented without the need for further processing. Generally, subjects can receive an intradermal injection of an effective amount of the MAGE-A3 HLA class II binding peptide. Initial doses can be followed by booster doses, following immunization protocols standard in the art.

A preferred method for facilitating incorporation of MAGE-A3 HLA class II binding peptides into HLA class II presenting cells is by expressing in the presenting cells a polypeptide which includes an endosomal targeting signal fused to a MAGE-A3 polypeptide which includes the class II binding peptide. Particularly preferred are MAGE-A3 fusion proteins which contain human invariant chain Ii.

Any of the foregoing compositions or protocols can include also MAGE HLA class I binding peptides for induction of a cytolytic T lymphocyte response. For example, as demonstrated below, the MAGE-A3 protein can be processed in a cell to produce both HLA class I and HLA class II responses. Several such peptides have been described in U.S. Pat. Nos. 5,585,461 and 5,591,430, and PCT published application PCT/US95/03657, as well as by Gaugler et al. (*J. Exp. Med*. 179:921-930, 1994), van der Bruggen et al. (*Eur. J. Immonol*. 24:3038-3043, 1994), and Herman et al. (*Immunogenetics* 43:377-383, 1996). By administering MAGE-A3 peptides which bind HLA class I and class II molecules (or nucleic acid encoding such peptides), an improved immune response may be provided by inducing both T helper cells and T killer cells.

In addition, non-MAGE-A3 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in the foregoing MAGE-A3 compositions and vaccines.

Especially preferred are nucleic acids encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol*. 15:1280-1284, 1997), with or without the natural flanking sequences, and can be separated by unrelated linker sequences if desired. The polytope is processed to generated individual epitopes which are recognized by the immune system for generation of immune responses.

Thus, for example, MAGE-A3 HLA class II binding peptides can be combined with peptides from other tumor rejection antigens (e.g. by preparation of hybrid nucleic acids or polypeptides) and with MAGE-A3 HLA class I binding peptides (some of which are listed below) to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in published PCT application WO 00/20581 (PCT/US99/21230).

Other examples of HLA class I and HLA class II binding peptides will be known to one of ordinary skill in the art (for example, see Coulie, *Stem Cells* 13:393-403, 1995), and can be used in the invention in a like manner as those disclosed herein. One of ordinary skill in the art can prepare polypeptides comprising one or more MAGE-A3 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13): 5845-5849, 1995; Gilbert et al., *Nature Biotechnol*. 15(12): 1280-1284, 1997; Thomson et al., *J. Immunol*. 157(2):822-826, 1996; Tam et al., *J. Exp. Med*. 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol*. 26(8):1951-1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As part of the immunization compositions, one or more substances that potentiate an immune response are administered along with the peptides described herein. Such substances include adjuvants and cytokines. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol. Cells* 7:178-186, 1997); incomplete Freund's adjuvant; complete Freund's adjuvant; montanide; immunostimulatory oligonucleotides (see e.g. CpG oligonucleotides described by Kreig et al., *Nature* 374:546-9, 1995); vitamin E and various water-in-oil emulsions prepared from biodegradable oils such as squalene and/or tocopherol. Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432-1434, 1995), GM-CSF and IL-18. Thus cytokines can be administered in conjunction with antigens and adjuvants to increase the immune response to the antigens. There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284-6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol*. 154:5637-5648, 1995). Tumor cell transfection with B7 has been discussed in relation to in vitro CTL expansion for adoptive transfer immunotherapy by Wang et al. (*J. Immunother*. 19:1-8, 1996). Other delivery mechanisms for the B7 molecule would include nucleic acid (naked DNA) immunization (Kim et al., *Nature Biotechnol*. 15:7:641-646, 1997) and recombinant viruses such as adeno and pox (Wendtner et al., *Gene Ther*. 4:726-735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloffet al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol*., 158:637-642, 1997; Fenton et al., *J. Immunother*., 21:95-108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the MAGE-A3 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 miligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Antigens encoded by MAGE-A3 and recognized by T cells are interesting targets for tumor immunotherapy because they are strictly tumor-specific and shared by many tumors of various histological types. A number of MAGE-A3 antigenic peptides presented by HLA class I molecules have been used in clinical trials and regressions of melanoma metastasis have been observed. We report here the identification of additional MAGE-A3 epitopes, including ACYEFLWGPRALVETS (MAGE-A3$_{267-282}$; SEQ ID NO:4) and GSDPACYEFLWGPRAL (MAGE-A3$_{263-278}$; SEQ ID NO:3), presented to CD4$^+$ T lymphocytes by HLA-DR1 molecules, which are expressed in approximately 18% of Caucasians and 6% of Orientals. These new epitopes may be useful both for therapeutic vaccination and for the evaluation of the immune response in cancer patients. To identify th epitopes, monocyte-derived dendritic cells from a cancer patient were loaded with a recombinant MAGE-A3 protein and used to stimulate autologous CD4$^+$ T cells. This patient had melanoma metastases expressing MAGE-A3 and was injected with a recombinant MAGE-A3 protein.

Materials and Methods

Cell lines, media, and reagents. The Epstein Barr Virus-transformed B (EBV-B) cell lines and the tumor cell lines MZ2-MEL43, NA41-MEL and SK37-MEL were cultured in IMDM (GIBCO BRL, Gaithersburg, Md.) supplemented with 10% fetal calf serum (GIBCO BRL), 0.24 mM L-asparagine, 0.55 mM L-arginine, 1.5 mM L-glutamine (AAG), 100 U/ml penicillin and 100 µg/ml streptomycin. Human recombinant IL-2 was purchased from Eurocetus (Amsterdam, The Netherlands), IL-7 from Genzyme (Cambridge, Mass.), GM-CSF from Schering Plough (Brinny, England), TNF-α from R&D Systems (Abingdon, United Kingdom). Human recombinant IL-4, IL-6, and IL-12 were produced in our laboratory.

The PhoenixAMPHO cell line (kindly provided by Dr. Nolan, Stanford University School of Medicine, CA, USA) is a high titer amphotropic retrovirus producing cell line that has been generated by stable transfection of 293T cells with a Moloney GagPol-IRES-Lyt 2 construct with an RSV promoter and a pPGK hygro selectable marker. These cells were then stably transfected with the Moloney amphotropic envelope gene driven by a CMV promoter and co-selected with the diphtheria toxin resistance gene (pHED-7). This producer cell line is helper virus free.

PhoenixAMPHO cells were cultured and passaged in 175 cm$^2$ flasks in DMEM (Life Technologies, Ghent, Belgium) supplemented with 10% heat inactivated FCS, 2 mM L-glutamine, 100 U/ml penicillin and 100 µg/ml streptomycin.

MAGE-A3 proteins. Two different MAGE-A3 proteins were used. One was produced in our laboratory in *Spodoptera frugiperda* (Sf9) insect cells, hereafter referred to as protein MAGE-A3$^{insect}$. A baculovirus expression system from PharMingen (San Diego, Calif.) was used. The coding sequence of MAGE-A3 was cloned in pAcGP67-A (PharMingen), a baculovirus transfer vector, downstream of the signal sequence of the gp67 surface protein of *Autographa californica* nuclear polyhedrosis virus (Ac-NPV), a strain of baculovirus. For easier purification, a sequence encoding a histidine tail was added at the C-terminus of the sequence of MAGE-A3. DNA of the recombinant plasmid was co-transfected with DNA of lethally mutated AcNPV into Sf9 insect cells. Co-transfection allows recombination between homologous regions of the plasmid and the virus, transferring the foreign gene from the vector to the AcNPV DNA.

Purification of the protein contained in the supernatant of Sf9 insect cell cultures involved the following steps: anion exchange on DEAE-sephadex A-50 (Amersham-Pharmacia Biotech AB, Uppsala, Sweden), retention on HighTrap chelating column (Amersham-Pharmacia Biotech AB, Uppsala, Sweden), retention on HighTrap chelating column (Amersham-Pharmacia Biotech AB, Uppsala, Sweden) saturated with NiCl$_2$, affinity chromatography with immobilized antibody 57B (kindly provided by Dr. G. Spagnoli, Department of Surgery, Basel, Switzerland), concentration and dialysis. The purification of the MAGE-A3 protein was monitored using a particle counting immunoassay, where the latex beads were coated with purified F(ab')$_2$ obtained from a goat immunized against MAGE-A3.

The other MAGE-A3 protein, hereafter referred to as protein MAGE-A3$^{bacteria}$, was produced in *Escherichia coli* by SmithKline-Beecham Biologicals (Rixensart, Belgium). MAGE-A3$^{bacteria}$ was produced as a recombinant His-MAGE-A3 protein (MAGE-A3 with a His tag) or as a recombinant LipoD-MAGE-A3-His protein. LipoD-MAGE-A3-His contains one third of the lipidic form of the *Haemophilus influenzae* protein at its N-terminal residue and a polyhistidine marker at its C-terminal residue. The proteins were purified by standard chromatographic procedures.

Construction the retrovirus encoding Ii-MAGE-A3. A recombinant retrovirus, pMFG-Ii80-MAGE-A3-(IRES)-ΔLNGFr was constructed (retro-Ii-MAGE). The sequence encoding a truncated form of the human low affinity nerve growth factor receptor (ΔLNGFr) was amplified from plasmid pUC19-ΔLNGFr that was kindly provided by Dr. C. Traversari (Instituto Scientifico H. S. Raffaele, Milan, Italy). The PCR amplification was carried out using the following primers:

sense: 5'-CCCTCATGAGGGCAGGTGCCACCG-3'(SEQ ID NO:17)

antisense: 5'-CCCAGATCTCTAGAGGATTCCCCT-GTTCCAC-3' (SEQ ID NO:18)

This PCR introduces a BspH1 site at the start codon and a Bgl2 site downstream from the stop codon. A BamH1 site near the 3' end was deleted. The PCR product was cloned in pCR2.1 and sequenced. The ΔLNGFr gene fragment was isolated from this vector as a BspH1-Not1 (from the pCR2.1 polylinker) fragment.

The IRES sequence derived from the encephalomyocarditis virus was transferred from pGEM-EMC2 (kindly provided by Dr. J.-C. Renauld, Catholic University of Louvain, Brussels, Belgium) into pBluescript. An EcoR1-Nco1 fragment from pBluescript-IRES was used for further construction.

Both the ΔNGFr and the IRES DNA fragments were ligated, together into pCR2.1 EcoR1-Not1. This three fragment ligation resulted in a plasmid naned pCR2.1-IRES-ΔLNGFr.

The IRES-ΔLNGFr sequence was then transferred into pMFG-Ii80, which encodes the first 80 amino acids of the human invariant chain (Ii80). A complete MAGE-A3 cDNA was then ligated downstream of Ii80 into pMFG-Ii80-(IRES)-ΔLNGFr to form pMFG-Ii80-MAGE-A3-(IRES)-ΔLNGFr, allowing the simultaneous expression of the Ii-MAGE-A3 fusion protein and the ΔLNGF receptor. The procedure for transducing cell lines has been described previously.

High titer MAGEA3-encoding recombinant retrovirus stocks were generated by introducing plasmid pMFG-Ii80-MAGE-A3-(IRES)-ΔLNGFr into PhoenixAMPHO packaging cells by transfection, as described below. Retrovirus stocks were harvested and used for transduction as described below.

Generation of high titer MAGE-A3 encoding recombinant retrovirus. The MAGE-A3 encoding retroviral vector plasmid pMFG-Ii80-MAGE-A3-(IRES)-ΔLNGFr was introduced into the PhoenixAMPHO packaging cells by transfection. The MFG retroviral vector is derived from Moloney murine leukemia virus and is lacking in a drug resistance marker nor does it express any other potential antigenic protein except for the inserted cDNA (Rivière, *Proc. Natl Acad. Sci. USA* 92:6733-6737, 1995). The transfection procedure is a modification of the calcium phosphate-mediated transfection protocol of Graham and van der Eb (*Virology* 54:536-539).

Twenty four hours prior to transfection, $10.8 \times 10^6$ PhoenixAMPHO cells were plated in 14 ml cell growth medium in a 75 cm$^2$ tissue culture flask (Falcon). After adding the cells, the flask was gently shaken forward and backward to distribute cells evenly about the flask bottom. The cells were incubated at 37° C. and 5% CO$_2$. At the time of transfection, when the cells should have reached a confluence of 70-80%, the medium was removed and was replaced by 14 ml fresh PhoenixAMPHO cell growth medium containing 25 mM chloroquine (Sigma Chemical Co., St. Louis, Mo., USA). A transfection cocktail was prepared in a 50 ml tube by adding 40 μg retroviral vector plasmid DNA to water and diluting to 1575 μl final volume. To this DNA solution 225 μl of 2 M CaCl$_2$ (Sigma) was added. Then, 1800 μl of 2×HeBS (50 mM HEPES, 10 mM KCl, 12 mM dextrose, 280 mM NaCl and 1.5 mM Na$_2$HPO$_4$ dissolved in distilled water, filtered through 0.2 μ filter and stored at −20° C.) was added dropwise to the DNA/CaCl$_2$ solution by vigorously bubbling for 15 seconds with an automatic pipette. The DNA/CaCl$_2$/HeBS mix was added immediately and dropwise onto the cells and the flask was gently swirled to ensure uniform mixing of DNA/CaPO$_4$ particles. The cells were incubated at 37° C./5% CO$_2$ for 7 to 9 hours and the chloroquine containing medium was changed for fresh PhoenixAMPHO cell growth medium. Approximately 24 hours prior to the harvest of the retroviral supernatant, the PhoenixAMPHO medium was removed and gently replaced by 9 ml of EBV cell growth medium (Iscove's) containing only 2.5% FCS. The retroviral supernatant was harvested 48 hours following transfection by removing the medium from the cells and filtering through a 0.45 μ filter to remove cell debris. After harvest and filtration, the virus containing medium was kept on ice, aliquoted in appropriate volumes in 15 ml polypropylene tubes and stored at −80° C.

Retroviral transduction of EBV cell lines. The EBV transformed cells were infected by resuspending the cells in an infection cocktail and centrifugation. Target cells were resuspended in 60 mm tissue culture plates (Falcon) at a density of $1.0 \times 10^6$ cells in 4 ml infection cocktail. The plates were centrifuged for 2 hours at 32° C. and 1200 rcf in an IEC centrifuge, rotor type 228. For each plate to be transduced, 4 ml of injection cocktail was prepared by diluting the viral supernatant 1:2 in EBV cell growth medium and adding protamine sulfate to a final concentration of 6 μg/ml. Centrifugation was followed by another 2 hours of incubation in a humidified incubator at 37° C. and cells were transferred to 4 ml of target cell growth medium. This transduction cycle was carried out immediately after plating the cells and was repeated at 24 and 48 hours.

Dendritic cells and CD4$^+$ responder T cells. Blood cells were collected as buffy-coat preparations from melanoma patient DDHK2, and processed essentially as described previously in PCT/US99/21230. Briefly, peripheral blood mononuclear cells (PBMC) were isolated by centrifugation on Lymphoprep (Nycomed Pharma, Oslo, Norway). In order to minimize contamination of PBMC by platelets, the preparation was first centrifuged for 20 min/1000 rpm at room temperature. After removal of the top 20-25 ml, containing most of the platelets, the tubes were centrifuged for 20 min/1500 rpm at room temperature. PBMC were depleted of T cells by rosetting with 2-aminoethylisothiouronium (Sigma) treated sheep erythrocytes. The lymphocyte-depleted PBMC were left to adhere for 2 hours at 37° C. in culture flasks (Falcon) at a density of $2 \times 10^6$ cells/ml in RPMI 1640 medium supplemented with L-asparagine (0.24 mM), L-arginine (0.55 mM), L-glutamine (1.5 mM) and 1% autologous serum (complete medium). Non-adherent cells were discarded.

Adherent cells (dendritic cells) were obtained by culturing monocytes in the presence of IL-4 (200 U/ml) and GM-CSF (70 ng/ml) in RPMI 1640 medium supplemented with AAG and 1% autologous plasma. One fourth of the medium was replaced by fresh medium and cytokines every two days. On day 7, the non-adherent cell population was used as a source of enriched dendritic cells. Rosetted T cells were treated with NH$_4$Cl (160 mM) to lyse the sheep erythrocytes, and washed. CD4$^+$ T lymphocytes were isolated from rosetted T cells by positive selection using an anti-CD4 monoclonal antibody coupled to magnetic microbeads (Miltenyi Biotech, Germany) and by sorting through a MACS, as recommended by the manufacturer Mixed lymphocytes/dendritic cells culture. Dendritic cells ($5 \times 10^5$) were incubated at 37° C., 5% CO$_2$, for 20 h in complete RPMI medium supplemented with IL-4, GM-CSF and TNF-α (5 ng/ml) in the presence of MAGE-A3$^{bacteria}$ (20 μg/ml). Cells were washed and added at $10^4$ per round-bottomed microwell to $10^5$ CD4$^+$ T lymphocytes in 200 μl IMDM supplemented with AAG and 1% autologous plasma in the presence of IL-6 (1,000 U/ml) and IL-12 (10 ng/ml). The CD4$^+$ lymphocytes were restimulated on days 7, 14, 21 and 28 with autologous dendritic cells freshly loaded with MAGE-A3$^{bacteria}$ and grown in IMDM supplemented with AAG and 1% autologous plasma (hereafter referred to as complete IMDM) supplemented with IL-2 (10 U/ml) and IL-7 (5 ng/ml). Aliquots of each microculture (~5,000 cells) were assessed on days 35 and 42 for their capacity to produce IFN-γ when stimulated with ~20,000 autologous EBV-B cells loaded for 20 h with either 20 μg/ml of MAGE-A3$^{bacteria}$, MAGE-A3$^{insect}$, or ovalbumin. After 20 h of co-culture in round-bottom microwells and in 100 μl complete IMDM medium supplemented with IL-2 (25 U/ml), IFN-γ released in the supernatant was measured by ELISA using reagents from Medgenix Diagnostics-Biosource (Fleurus, Belgium).

CD4$^+$ T cell clones. Cells from positive microculture F4 that were cloned by limiting dilution, using irradiated autologous EBV-B cells transduced with retro-Ii.MAGE-A3 (5×10$^3$-2×10$^4$ cells) as stimulator cells. Irradiated allogeneic LG2-EBV cells (5×10$^3$-10$^4$) were used as feeder cells. CD4$^+$ T cell clones were supplemented once a week with fresh culture medium in the presence of IL-2 (50 U/ml), IL-7 (5 ng/ml) and IL-4 (5 U/ml).

Recognition assays with peptides. Peptides were synthesized on solid phase using F-moc for transient NH2-terminal protection and were characterized using mass spectrometry. All peptides were >90% pure, as indicated by analytical HPLC. Lyophilized peptides were dissolved at 5 mg/ml in 10 mM acetic acid and 10% DMSO, and stored at -20° C. EBV-B cells were distributed at 20,000 cells per round-bottomed microwell and incubated for 2 h at 37° C. in the presence of the different peptides, the indicated concentrations representing their concentrations during the incubation step. CD4$^+$ T lymphocytes (5,000) were added in 100 μl of complete IMDM (GIBCO) medium supplemented with IL-2 (25 U/ml). Supernatants were harvested after 20 h of co-culture and IFN-γ production was measured by ELISA.

Recognition of tumor cells. Tumor cells were distributed at 20,000 cells per round-bottomed microwell together with 5,000 CD4$^+$ T lymphocytes in 100 μl of complete IMDM medium in the presence of IL-2 (25 U/ml). Supernatants were harvested after 20 h of co-culture and the IFN-γ production was measured by ELISA.

Results

To identify new MAGE-A3 epitopes presented by HLA class II molecules, monocyte-derived dendritic cells (DC) from melanoma patient DDHK2 were cultured in autologous plasma and incubated overnight with a recombinant MAGE-A3 protein and with TNF-α to induce their maturation. These cells were then used to stimulate autologous CD4$^+$ T lymphocytes. In previous experiments, a large number of the CD4$^+$ T cell clones obtained with the same method were apparently directed against bacterial contaminants in the batch of protein. Therefore, a MAGE-A3 protein produced in *Escherichia coli* (MAGE-A3$^{bacteria}$) was used to stimulate the lymphocytes, and a MAGE-A3 protein produced in *Spodoptera frugiperda* insect cells (MAGE-A3$^{insect}$) to test the specificity of the responder lymphoctyes (data not shown).

A CD4$^+$ T cell clone directed against a MAGE-A3 antigen. A total of 96 microcultures were set up, each containing 10$^5$ CD4$^+$ cells and 10$^4$ autologous stimulator DC loaded with protein MAGE-A3$^{bacteria}$ as stimulator cells. Responder cells were restimulated three times at weekly intervals with DC loaded with the protein. After a resting period of two weeks, responder cells of each microculture were tested on days 35 and 42 for IFN-γ production after stimulation with autologous EBV-B cells loaded with either MAGE-A3$^{insect}$, MAGE-A3$^{bacteria}$, or ovalbumin. Twelve microcultures specifically produced a high level of IFN-γ after stimulation with protein MAGE-A3$^{insect}$ and protein MAGE-A3$^{bacteria}$. One of them, F4, was cloned by limiting dilution using autologous EBV-B cells transduced with retro-Ii.MAGE-A3 as stimulator cells. Several positive clones were obtained, including CD4$^+$ T cell clone MAGJ569/F4.3. This clone recognized autologous EBV-B cells loaded with either protein MAGE-A3$^{insect}$ or protein MAGE-A3$^{bacteria}$, or EBV-B cells transduced with retro Ii.MAGE-A3.

Autologous DDHK2-EBV-B cells were pulsed for 20 h with 20 μg/ml of protein MAGE-A3$^{insect}$ or protein MAGE-A3$^{bacteria}$. Protein-pulsed EBV-B cells (20,000) or EBV-B cells transduced with a retrovirus encoding a fusion protein composed of MAGE-A3 and a truncated human invariant chain (retro-Ii.MAGE-A3) were incubated for 20 h in microwells with CD4$^+$ clone MAGJ569/F4.3 cells (5,000). IFN-γ production was measured by ELISA (FIG. 1). The results shown represent the average of triplicate cultures.

Clone MAGJ569/F4.3 recognized peptide ACYEFLWG-PRALVETS (SEQ ID NO:4). A set of peptides of 16 amino acids, which overlapped by 12 and covered the entire MAGE-A3 protein sequence, was screened: autologous EBV-B cells were pulsed with each of these peptides and tested for recognition by clone MAGJ569/F4.3. It produced IFN-γ after stimulation with two overlapping peptides, namely MAGE-A3$_{263-278}$ (GSDPACYEFLWGPRAL; SEQ ID NO:3) and MAGE-A3$_{267-282}$ (ACYEFLWGPRALVETS; SEQ ID NO:4).

DDHK EBV-B cells (20,000) were incubated in microwells for 2 hours with different concentrations of the MAGE-A3 peptides. IFN-γ production was measured by ELISA after 20 hours of coculture with CD4$^+$ clone MAGJ569/F4.3 (5,000 cells) (FIG. 2). The experiments were performed twice.

FIG. 2A shows Experiment I. A number of MAGE-A3 peptides of different lengths were tested and recognized by clone MAGJ569/F4.3. The peptides tested were GSDPA-CYEFLWGPRAL (MAGE-A3$_{263-278}$; SEQ ID NO:3), ACYEFLWGPRALVETS (MAGE-A3$_{267-282}$; SEQ ID NO:4), ACYEFLWGPRALVE (SEQ ID NO:7), ACYEFL-WGPRALV (SEQ ID NO:8), ACYEFLWGPRAL (SEQ ID NO:9), ACYEFLWGPRA (SEQ ID NO:10), ACYEFL-WGPR (SEQ ID NO:11), CYEFLWGPRALVE (SEQ ID NO:12), YEFLWGPRALVE (SEQ ID NO:13), and EFL-WGPRALVE (SEQ ID NO:14). Of these, GSDPACYEFL-WGPRAL (SEQ ID NO:3), ACYEFLWGPRALVETS (SEQ ID NO:4), and ACYEFLWGPRALVE. (SEQ ID NO:7) were well recognized. It is expected that ACYEFLWGPRALVET (SEQ ID NO:16), as intermediate between the amino acid sequences of SEQ ID NO:4 and SEQ ID NO:7, also would be well recognized.

FIG. 2B shows Experiment II. For this second experiment, concentration of peptides were measured by optical density. The peptides tested were GSDPACYEFLWGPRAL (SEQ ID NO:3), ACYEFLWGPRALVETS (SEQ ID NO:4), ACYEFLWGPRALVE (SEQ ID NO:7) and ACYEFLWG-PRALV (SEQ ID NO:8). Of these, GSDPACYEFLWG-PRAL (SEQ ID NO:3), ACYEFLWGPRALVETS (SEQ ID NO:4), and ACYEFLWGPRALVE (SEQ ID NO:7) were well recognized, while ACYEFLWGPRALV (SEQ ID NO:8) was recognized but only at higher concentrations of peptide.

Figure 3:
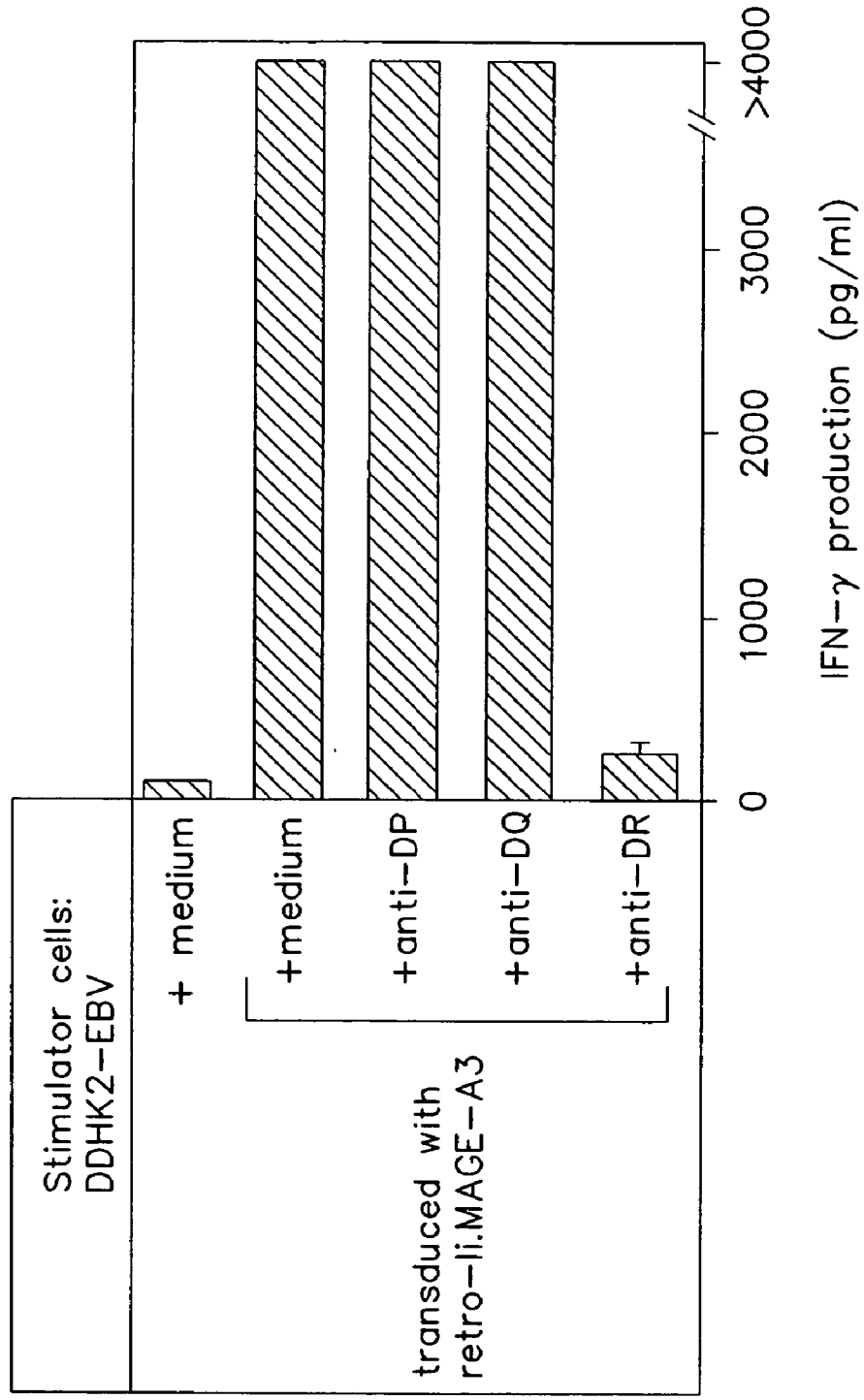
FIG. 3 is a graph showing that the MAGE-A3 peptide is presented to CD4+ clone MAGJ569/F4.3 by HLA-DR molecules

The peptide is presented by HLA-DR1 molecules. DDHK2-EBV transduced with retro-Ii.MAGE-A3 (20,000) were cocultured for 20 hours with CD4$^+$ clone MAGJ569/F4.3 cells (5,000), in the presence of either monoclonal antibody B7.21 (anti-DP), SPV L3 (anti-DQ), or AH89 (anti-DR). IFN-γ production was measured by ELISA. The recognition by clone MAGJ569/F4.3 of autologous EBV-B cells loaded with peptide MAGE-A3$_{267-282}$ (ACYEFLWGPRALVETS; SEQ ID NO:4) was abolished by an anti-HLA-DR antibody, but not by antibodies against HLA-DP or HLA-DQ (FIG. 3).

Melanoma patient DDHK2 was typed HLA-DR1, DR15 and DR51. Peptide ACYEFLWGPRALVETS (SEQ ID NO:4) was loaded on several EBV-B cell lines expressing DR1, DR15 or DR51. All and only those expressing DR1 were able to present the peptide to clone MAGJ569/F4.3 (Table 1). Autologous DDHK2-EBV and allogeneic EBV-B cells (20,000) were incubated for 1 hour with 5 μg/ml of peptide ACYEFLWGPRALVETS (MAGE-A3$_{267-282}$; SEQ ID NO:4) and washed. Peptide-pulsed EBV-B cells (20,000) were then incubated with CD4$^+$ clone MAGJ565/F4.3 cells (5,000). IFN-γ production was measured by ELISA after 20 hours of co-culture.

TABLE 1

Presentation of the MAGE-A3 peptide (MAGE362) by HLA-DR1 cells

| EBV-B cell line | Serological specificity | IFN-γ production (pg/ml) |
|---|---|---|
| | DR1 positive | |
| DDHK2 | DR1 DR15 DR51 | >4000 |
| LB1158 | DR1 DR13 DR52 | 2439 |
| LB831 | DR1 DR7 DR53 | 2037 |
| LB2138 | DR1 DR13 | 1810 |
| | DR1 negative | |
| LB650 | DR7 DR15 DR51 DR53 | 83 |
| LB1870 | DR15 DR53 DR7 | 88 |
| LB1856 | DR15 | 49 |
| LB2095 | DR13 DR15 DR51 DR52 | 22 |

Recognition of tumor cell lines. Three DR1 melanoma cell lines expressing MAGE-A3 were tested for their ability to stimulate CD4$^+$ T cell clone MAGJ569/F4.3 to produce IFN-γ. Tumor cells were pretreated for 48 h with 100 U/ml of IFN-γ and were pulsed in microwells (20,000) for 1 h with 1 μg/ml of peptide ACYEFLWGPRALVETS (MAGE-A3$_{267-282}$; SEQ ID NO:4). IFN-γ production was measured by ELISA after 20 h of coculture with CD4$^+$ clone MAGJ610/F4.3 (5,000). Autologous EBV-stimulator cells transduced with a retrovirus encoding Ii.MAGE-A3 were used as positive controls.

Figure 4:
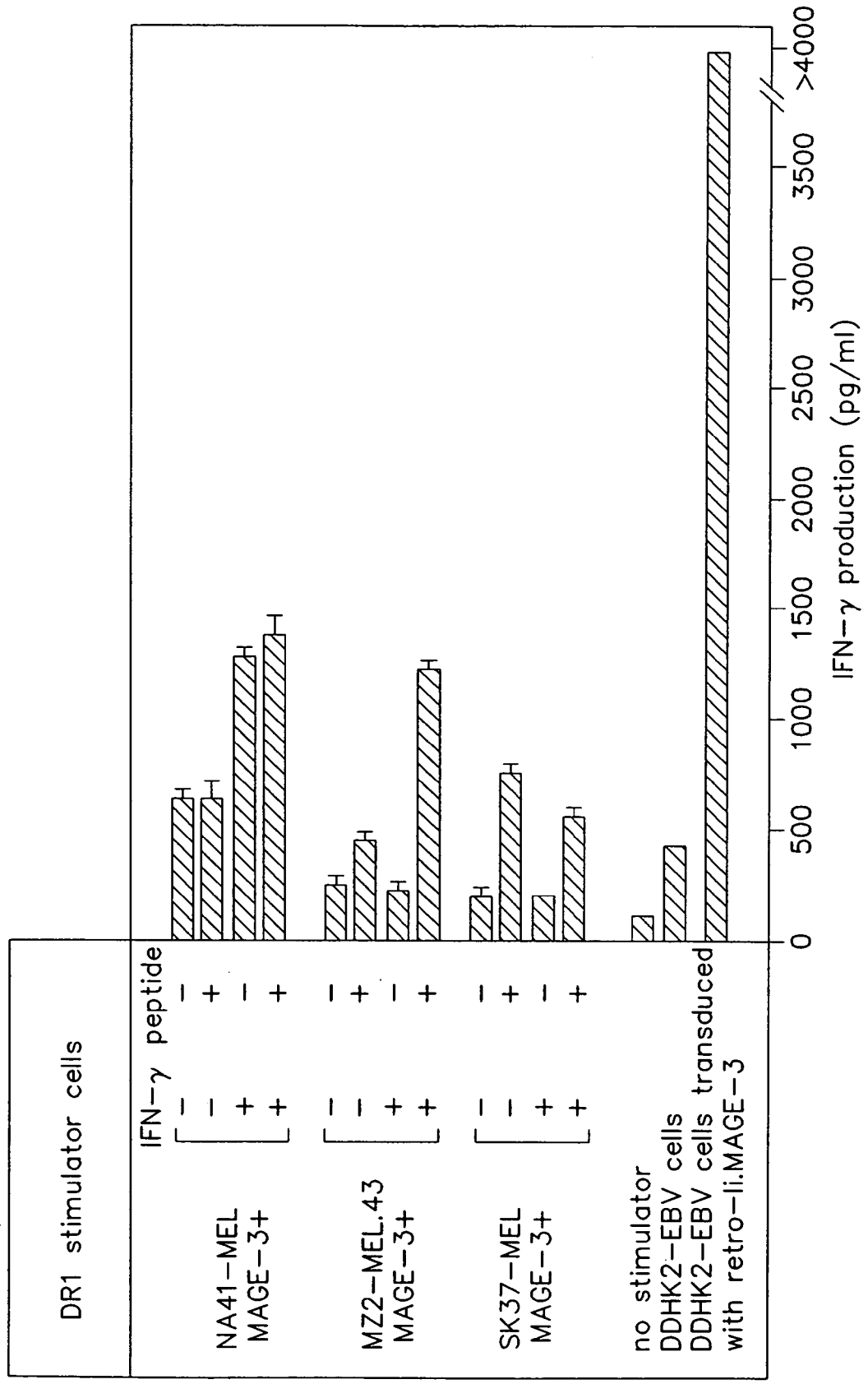
FIG. 4 is a graph depicting recognition of DR1 tumor cells expressing MAGE-A3 by CD4+ clone MAGJ569/F4.3.

One of the melanoma cell lines, NA41-MEL, slightly stimulated the CD4$^+$ clone MAGJ569/F4.3 to produce IFN-γ (FIG. 4). Treatment of this cell line with IFN-γ improved its recognition.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid encoding a MAGE-A3 HLA class II-binding peptide that consists of a fragment of SEQ ID NO:2, wherein the fragment comprises an amino acid sequence selected from the group consisting of SEQ ID NO:3, SEQ ID NO:4 and SEQ ID NO:7, wherein the MAGE-A3 HLA class II binding peptide includes up to 7 amino acids of SEQ ID NO:2 consecutive to the N-terminus and/or the C-terminus of SEQ ID NOs:3, 4 or 7.

2. The isolated nucleic acid of claim 1, wherein the MAGE-A3 HLA class II-binding peptide includes up to 5 amino acids of SEQ ID NO:2 consecutive to the N-terminus and/or the C-terminus of SEQ ID NO:3, SEQ ID NO:4 or SEQ ID NO:7.

3. The isolated nucleic acid of claim 1, wherein the MAGE-A3 HLA class II-binding peptide consists of an amino acid sequence selected from the group consisting of SEQ ID NO:3, SEQ ID NO:4, SEQ ID NO:7 and SEQ ID NO:16.

4. The isolated nucleic acid of claim 3 wherein the MAGE-A3 HLA class II-binding peptide consists of the amino acid sequence set forth as SEQ ID NO:4.

5. An isolated nucleic acid comprising a nucleotide sequence encoding an endosomal targeting signal linked to the isolated nucleic acid of claim 1.

6. The isolated nucleic acid of claim 5, wherein the endosomal targeting signal comprises an endosomal targeting portion of human invariant chain Ii.

7. The isolated nucleic acid of claim 1, wherein the nucleic acid comprises a nucleotide sequence selected from the group consisting of SEQ ID NO:5, SEQ ID NO:6 and SEQ ID NO:15.

8. An isolated nucleic acid comprising a nucleotide sequence encoding a MAGE-A3 HLA class I-binding peptide, linked to the isolated nucleic acid of any of claims 1-7.

9. An expression vector comprising the isolated nucleic acid of any of claims 1-7 operably linked to a promoter.

10. An expression vector comprising the isolated nucleic acid of claim 8 operably linked to a promoter.

11. The expression vector of claim 9, further comprising a nucleic acid that encodes a HLA-DR1 molecule.

12. The expression vector of claim 10, further comprising a nucleic acid that encodes a HLA-DR1 molecule.

13. An isolated host cell transfected or transformed with the expression vector of claim 9.

14. An isolated host cell transfected or transformed with the expression vector of claim 10.

15. An isolated host cell transfected or transformed with the expression vector of claim 11.

16. An isolated host cell transfected or transformed with the expression vector of claim 12.

17. The host cell of claim 13, wherein the host cell expresses a HLA-DR1 molecule.

18. The host cell of claim 14, wherein the host cell expresses a HLA-DR1 molecule.

19. The host cell of claim 15, wherein the host cell expresses a HLA-DR1 molecule.

20. The host cell of claim 16, wherein the host cell expresses a HLA-DR1 molecule.

* * * * *